(12) United States Patent
Van Sciver

(10) Patent No.: US 8,927,050 B2
(45) Date of Patent: Jan. 6, 2015

(54) METHOD AND APPARATUS FOR COATING A STENT

(71) Applicant: Advanced Cardiovascular Systems, Inc., Santa Clara, CA (US)

(72) Inventor: Jason Van Sciver, Los Gatos, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 13/669,439

(22) Filed: Nov. 5, 2012

(65) Prior Publication Data

US 2013/0064966 A1  Mar. 14, 2013

Related U.S. Application Data

(62) Division of application No. 11/418,696, filed on May 4, 2006, now Pat. No. 8,304,012.

(51) Int. Cl.
| | | |
|---|---|---|
| *B05D 3/00* | (2006.01) | |
| *B05D 3/04* | (2006.01) | |
| *B05B 13/02* | (2006.01) | |
| *B05D 1/02* | (2006.01) | |
| *B05D 1/00* | (2006.01) | |
| *B05D 1/32* | (2006.01) | |

(52) U.S. Cl.
CPC .......... *B05D 3/0473* (2013.01); *B05B 13/0207* (2013.01); *B05B 13/0221* (2013.01); *B05B 13/0228* (2013.01); *B05D 1/02* (2013.01); *B05D 1/002* (2013.01); *B05D 1/32* (2013.01)
USPC .......................... 427/2.25; 427/2.1; 427/2.24

(58) Field of Classification Search
USPC ................. 427/2.1, 2.24, 2.25, 446, 448, 533
See application file for complete search history.

(56) References Cited

U.S. PATENT DOCUMENTS

| | | | |
|---|---|---|---|
| 3,419,062 A | 12/1968 | Petrus | |
| 3,758,960 A | 9/1973 | McCreary et al. | |
| 4,135,311 A | 1/1979 | Imbert | |
| 4,549,362 A | 10/1985 | Haried | |
| 5,642,571 A | 7/1997 | Park | |
| 6,214,115 B1 | 4/2001 | Taylor et al. | |
| 6,322,847 B1 | 11/2001 | Zhong et al. | |
| 6,562,136 B1 | 5/2003 | Chappa et al. | |
| 6,565,659 B1 * | 5/2003 | Pacetti et al. | 118/500 |
| 6,605,154 B1 | 8/2003 | Villareal | |

(Continued)

FOREIGN PATENT DOCUMENTS

| | | |
|---|---|---|
| EP | 1 518 570 | 3/2005 |
| WO | WO 95/27878 | 10/1995 |

OTHER PUBLICATIONS

Invitation to Pay Additional Fees for PCT/US2007/009115, filed Apr. 13, 2007, mailed Oct. 26, 2007, 10 pgs.

*Primary Examiner* — Dah-Wei D Yuan
*Assistant Examiner* — Hai Yan Zhang
(74) *Attorney, Agent, or Firm* — Squire Patton Boggs (US) LLP

(57) ABSTRACT

A method of coating a stent comprises contacting a first axial portion of a stent with a support element, such that a second axial portion does not contact the support element or any other support element, applying a coating material to the second axial portion, and inhibiting or preventing application of the coating material on the first axial portion. A shuttle sheath can be used to push the stent off the support element.

17 Claims, 26 Drawing Sheets

(56) References Cited

U.S. PATENT DOCUMENTS

| | | |
|---|---|---|
| 6,979,348 B2 | 12/2005 | Sundar |
| 7,137,993 B2* | 11/2006 | Acosta et al. ............... 623/1.11 |
| 7,175,874 B1* | 2/2007 | Pacetti ........................ 427/2.25 |
| 7,211,150 B1 | 5/2007 | Kokish et al. |
| 7,628,859 B1* | 12/2009 | Hossainy et al. ............. 118/500 |
| 8,007,856 B2 | 8/2011 | Hossainy et al. |
| 2003/0028240 A1* | 2/2003 | Nolting et al. ............... 623/1.13 |
| 2003/0059520 A1 | 3/2003 | Chen et al. |
| 2003/0099765 A1 | 5/2003 | Jayaraman |
| 2003/0204245 A1* | 10/2003 | Brightbill ................... 623/1.16 |
| 2004/0079354 A1 | 4/2004 | Takeda |
| 2004/0093061 A1* | 5/2004 | Acosta et al. ............... 623/1.11 |
| 2004/0187775 A1* | 9/2004 | Kerrigan ...................... 118/500 |
| 2004/0231183 A1 | 11/2004 | Makoto |
| 2004/0247775 A1* | 12/2004 | Boulais et al. ................ 427/2.1 |
| 2005/0010282 A1 | 1/2005 | Thornton et al. |
| 2005/0144806 A1 | 7/2005 | Yoshida |
| 2005/0202156 A1* | 9/2005 | O'Connor et al. ............ 427/2.1 |
| 2006/0038027 A1* | 2/2006 | O'Connor et al. ................ 239/8 |
| 2007/0212477 A1* | 9/2007 | Feng et al. .................... 427/2.1 |
| 2007/0231457 A1* | 10/2007 | Pham et al. .................... 427/2.1 |
| 2007/0259114 A1* | 11/2007 | Malone et al. ................. 427/271 |
| 2009/0032612 A1* | 2/2009 | Kunstmann et al. ....... 239/102.2 |

* cited by examiner

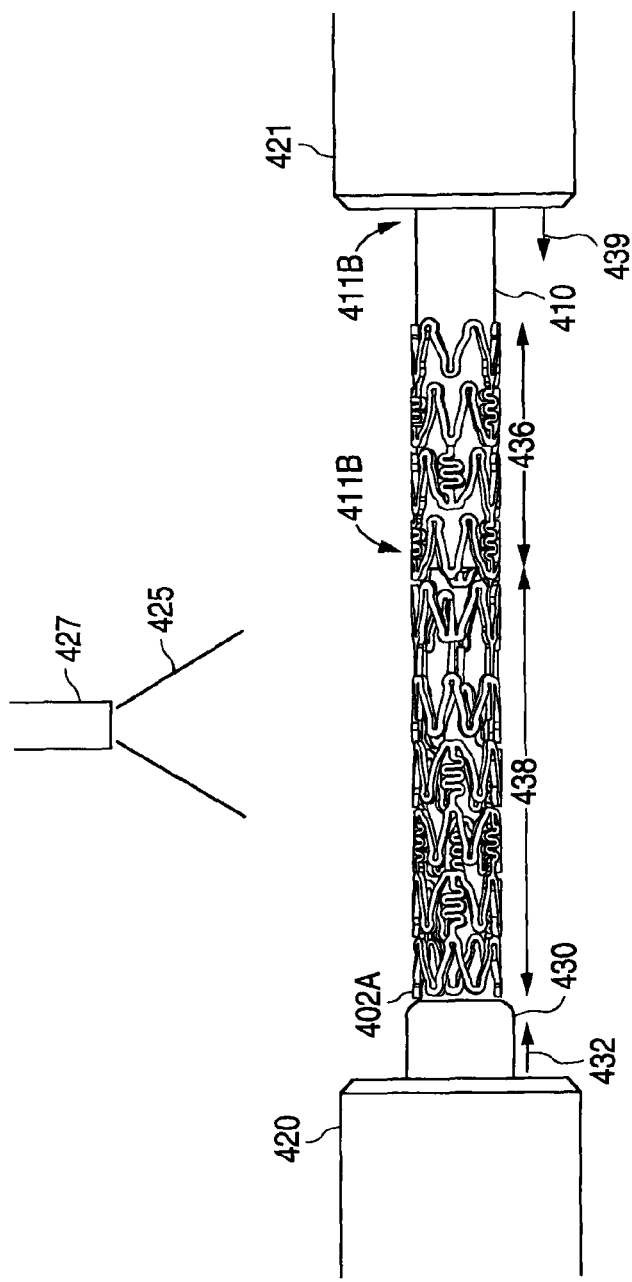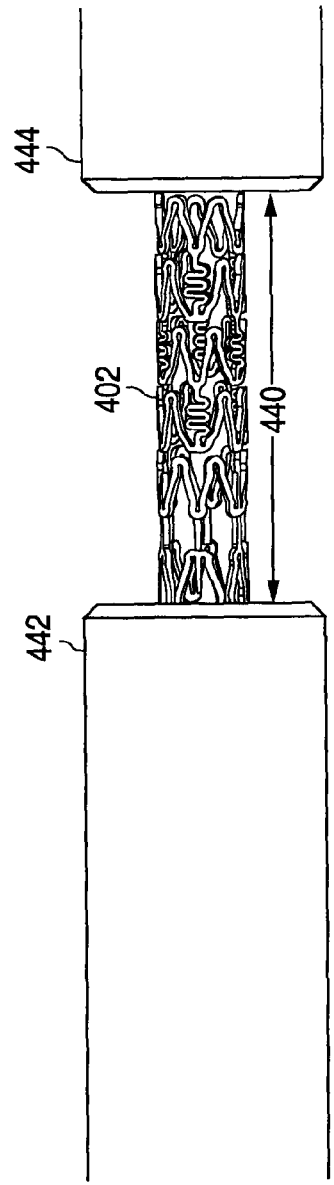
FIG. 17A
FIG. 18

METHOD AND APPARATUS FOR COATING A STENT

CROSS-REFERENCE TO RELATED APPLICATION

This application is a divisional of application Ser. No. 11/418,696, filed May 4, 2006, which is incorporated herein by reference.

BACKGROUND OF THE INVENTION

1. Field of the Invention

This invention relates to methods and devices for coating stents.

2. Description of the State of the Art

This invention relates to radially expandable endoprostheses, that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices, that function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Stents are typically composed of scaffolding that includes a pattern or network of interconnecting structural elements or struts, formed from wires, tubes, or sheets of material rolled into a cylindrical shape. This scaffolding gets its name because it physically holds open and, if desired, expands the wall of the passageway. Typically, stents are capable of being compressed or crimped onto a catheter so that they can be delivered to and deployed at a treatment site. Delivery includes inserting the stent through small lumens using a catheter and transporting it to the treatment site. Deployment includes expanding the stent to a larger diameter once it is at the desired location. Mechanical intervention with stents has reduced the rate of restenosis as compared to balloon angioplasty. Yet, restenosis remains a significant problem. When restenosis does occur in the stented segment, its treatment can be challenging, as clinical options are more limited than for those lesions that were treated solely with a balloon.

Stents are used not only for mechanical intervention but also as vehicles for providing biological therapy. Biological therapy uses medicated stents to locally administer a therapeutic substance. Effective concentrations at the treated site require systemic drug administration which often produces adverse or even toxic side effects. Local delivery is a preferred treatment method because it administers smaller total medication levels than systemic methods, but concentrates the drug at a specific site. Local delivery thus produces fewer side effects and achieves better results.

A medicated stent may be fabricated by coating the surface of a stent with an active agent or an active agent and a polymeric carrier. Those of ordinary skill in the art fabricate coatings by applying a polymer, or a blend of polymers, to the stent using well-known techniques. Such a coating composition may include a polymer solution and an active agent dispersed in the solution. The composition may be applied to the stent by immersing the stent in the composition or by spraying the composition onto the stent. The solvent then evaporates, leaving on the stent surfaces a polymer coating impregnated with the drug or active agent.

Accurately loading drugs, minimizing coating defects, and coating with pure coating materials favor improved coating quality. In addition, adequate throughput of the overall manufacturing process is also of concern.

SUMMARY OF THE INVENTION

Briefly and in general terms, the present invention is directed to a method and apparatus for coating a stent.

In aspects of the invention, a method comprises contacting a first axial portion of a stent with a support element such that a second axial portion of the stent does not contact the support element, followed by applying a coating material to the second axial portion while the second axial portion does not contact the support element, and during the applying of the coating material to the second axial portion, inhibiting or preventing application of the coating material on the first axial portion.

In aspects of the present invention, an apparatus comprises a support element having a free end for supporting a stent, a spray nozzle oriented to spray a coating material toward a stent supported by the free end of the support element, and a shuttle sheath coupled to support element and configured to push the stent off the support element with movement of the shuttle sheath relative to the free end of the support element.

The features and advantages of the invention will be more readily understood from the following detailed description which should be read in conjunction with the accompanying drawings.

BRIEF DESCRIPTION OF THE DRAWINGS

FIG. 17A depicts an alternative view of the stent support system of FIG. 15A.

FIG. 18 depicts an embodiment for coating a central portion of a stent that has no contact points.

DETAILED DESCRIPTION OF THE INVENTION

Embodiments of the present invention relate to coating implantable medical devices such as stents. More generally, embodiments of the present invention may also be used in coating devices including, but not limited to, self-expandable stents, balloon-expandable stents, stent-grafts, vascular grafts, cerebrospinal fluid shunts, pacemaker leads, closure devices for patent foramen ovale, and synthetic heart valves.

In particular, a stent can have virtually any structural pattern that is compatible with a bodily lumen in which it is implanted. Typically, a stent is composed of a pattern or network of circumferential and longitudinally extending interconnecting structural elements or struts. In general, the struts are arranged in patterns, which are designed to contact the lumen walls of a vessel and to maintain vascular patency. A myriad of strut patterns are known in the art for achieving particular design goals. A few of the more important design characteristics of stents are radial or hoop strength, expansion ratio or coverage area, and longitudinal flexibility. Embodiments of the present invention are applicable to virtually any stent design and are, therefore, not limited to any particular stent design or pattern. One embodiment of a stent pattern may include cylindrical rings composed of struts. The cylindrical rings may be connected by connecting struts.

In some embodiments, a stent may be formed from a tube by laser cutting the pattern of struts in the tube. The stent may also be formed by laser cutting a metallic or polymeric sheet, rolling the pattern into the shape of the cylindrical stent, and providing a longitudinal weld to form the stent. Other methods of forming stents are well known and include chemically etching a metallic or polymeric sheet and rolling and then welding it to form the stent.

In other embodiments, a metallic or polymeric filament or wire may also be coiled to form the stent. Filaments of polymer may be extruded or melt spun. These filaments can then be cut, formed into ring elements, welded closed, corrugated to form crowns, and then the crowns welded together by heat or solvent to form the stent.

Figure 1:
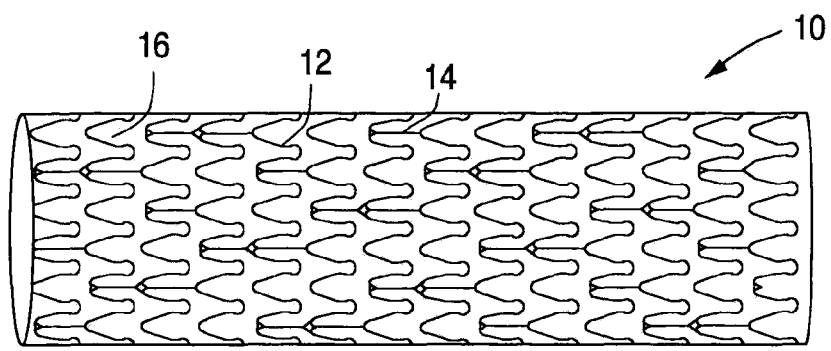
FIG. 1 depicts a three-dimensional view of a cylindrically-shaped stent.

FIG. 1 illustrates a conventional stent 10 formed from a plurality of struts 12. The plurality of struts 12 are radially expandable and interconnected by connecting elements 14 that are disposed between adjacent struts 12, leaving lateral openings or gaps 16 between adjacent struts 12. Struts 12 and connecting elements 14 define a tubular stent body having an outer, tissue-contacting surface and an inner surface.

The cross-section of the struts in stent 10 may be rectangular- or circular-shaped. The cross-section of struts is not limited to these, and therefore, other cross-sectional shapes are applicable with embodiments of the present invention. Furthermore, the pattern should not be limited to what has been illustrated as other stent patterns are easily applicable with embodiments of the present invention.

Coating a Stent

As indicated above, a medicated coating on a stent may be fabricated by spraying a coating composition including polymer and drug on the stent. Spray coating a stent typically involves mounting or disposing a stent on a support, followed by spraying a coating material from a nozzle onto the mounted stent.

A spray apparatus, such as EFD 780S spray device with VALVEMATE 7040 control system (manufactured by EFD Inc., East Providence, R.I., can be used to apply a composition to a stent. A EFD 780S spray device is an air-assisted external mixing atomizer. The composition is atomized into small droplets by air and uniformly applied to the stent surfaces. Other types of spray applicators, including air-assisted internal mixing atomizers and ultrasonic applicators, can also be used for the application of the composition.

To facilitate uniform and complete coverage of the stent during the application of the composition, the stent can be rotated about the stent's central longitudinal axis. Rotation of the stent can be from about 0.1 rpm to about 300 rpm, more narrowly from about 30 rpm to about 200 rpm. By way of example, the stent can rotate at about 150 rpm. The stent can also be moved in a linear direction along the same axis. The stent can be moved at about 1 mm/second to about 12 mm/second, for example about 6 mm/second, or for a minimum of at least two passes (i.e., back and forth past the spray nozzle).

A nozzle can deposit coating material onto a stent in the form of fine droplets. An atomization pressure of a sprayer can be maintained at a range of about 5 psi to about 30 psi. The droplet size depends on factors such as viscosity of the solution, surface tension of the solvent, and atomization pressure. The flow rate of the composition from the spray nozzle can be from about 0.01 mg/second to about 1.0 mg/second, for example about 0.1 mg/second. Only a small percentage of the composition that is delivered from the spray nozzle is ultimately deposited on the stent. By way of example, when a composition is sprayed to deliver about 1 mg of solids, only about 100 micrograms or about 10% of the solids sprayed will likely be deposited on the stent.

Depositing a coating of a desired thickness in a single coating stage can result in an undesirably nonuniform surface structure and/or coating defects. Therefore, the coating process can involve multiple repetitions of spraying forming a plurality of layers. Each repetition can be, for example, about 0.5 second to about 20 seconds, for example about 10 seconds in duration. The amount of coating applied by each repetition can be about 1 microgram/cm$^2$ (of stent surface) to about 50 micrograms/cm$^2$, for example less than about 20 micrograms/cm$^2$ per 1-second spray.

As indicated above, the coating composition can include a polymer dissolved in a solvent. Each repetition can be followed by removal of a significant amount of the solvent(s). In an embodiment, there may be less than 5%, 3%, or more narrowly, less than 1% of solvent remaining in the coating after drying between repetitions. When the coating process is completed, all or substantially all of the solvent may be removed from the coating material on the stent. Any suitable number of repetitions of applying the composition followed by removing the solvent(s) can be performed to form a coating of a desired thickness or weight. Excessive application of the polymer can, however, cause coating defects.

A stent coated with coating material can be dried by allowing the solvent to evaporate at room or ambient temperature. Depending on the volatility of the particular solvent employed, the solvent can evaporate essentially upon contact with the stent. Alternatively, the solvent can be removed by subjecting the coated stent to various drying processes. Drying time can be decreased to increase manufacturing throughput by heating the coated stent. For example, removal of the solvent can be induced by baking the stent in an oven at a mild temperature (e.g., 60° C.) for a suitable duration of time (e.g., 2-4 hours) or by the application of warm air. A stent is typically dried in an oven as the final drying step when the deposition stages are completed.

Evaporation of the solvent(s) can be induced by application of a warm gas between each repetition which can prevent coating defects and minimize interaction between the active agent and the solvent. The stent may be positioned below a nozzle blowing the warm gas. A warm gas may be particularly suitable for embodiments in which the solvent employed in the coating composition is a non-volatile solvent (e.g., dimethylsulfoxide (DMSO), dimethylformamide (DMF), and dimethylacetamide (DMAC)). The temperature of the warm gas can be from about 25° C. to about 200° C., more narrowly from about 40° C. to about 90° C. By way of example, warm gas applications can be performed at a temperature of about 60° C., at a flow speed of about 5,000 feet/minute, and for about 10 seconds.

The gas can be directed onto the stent following a waiting period of about 0.1 second to about 5 seconds after the application of the coating composition so as to allow the liquid sufficient time to flow and spread over the stent surface before the solvent(s) is removed to form a coating. The waiting period is particularly suitable if the coating composition contains a volatile solvent since such solvents are typically removed quickly. As used herein "volatile solvent" means a solvent that has a vapor pressure greater than 17.54 Torr at ambient temperature, and "non-volatile solvent" means a solvent that has a vapor pressure less than or equal to 17.54 Torr at ambient temperature.

Any suitable gas can be employed, examples of which include air, argon, or nitrogen. The flow rate of the warm gas can be from about 20 cubic feet/minute (CFM) (0.57 cubic meters/minute (CMM)) to about 80 CFM (2.27 CMM), more narrowly about 30 CFM (0.85 CMM) to about 40 CFM (1.13 CMM). The warm gas can be applied for about 3 seconds to about 60 seconds, more narrowly for about 10 seconds to about 20 seconds. By way of example, warm air applications can be performed at a temperature of about 50° C., at a flow rate of about 40 CFM, and for about 10 seconds.

Drying

Regardless of the method used for drying a stent, it is important for the drying process to be performed in a consistent manner for each layer and each stent. The same or similar processing conditions or parameters should exist for each layer of coating material applied for each stent. The reason for this is that drying process parameters can influence the molecular structure and morphology of a dried polymer and drug coating. Drug release parameters depend upon on molecular structure and morphology of a coating. Therefore, drug release parameters depend upon parameters of the drying process. For example, generally, the rate of a drying process is directly proportional to the resultant drug release rate of a resultant coating.

Since the temperature of a drying process is directly related to the rate of drying, it is important to control the drying temperature to obtain coating consistency. In general, the more consistent the temperature during the drying process from layer to layer and stent to stent, the more consistent the resultant coating in a given stent and from stent to stent.

Figure 2A:
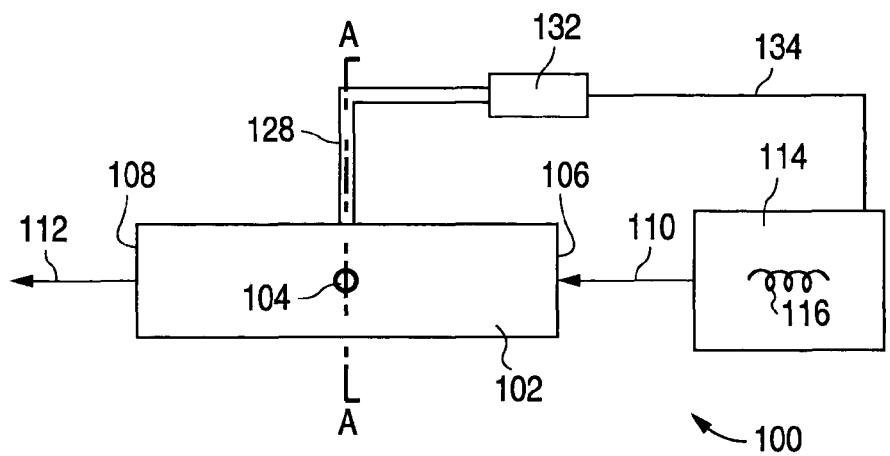
FIG. 2A depicts a schematic embodiment of a drying apparatus.
Figure 2B:
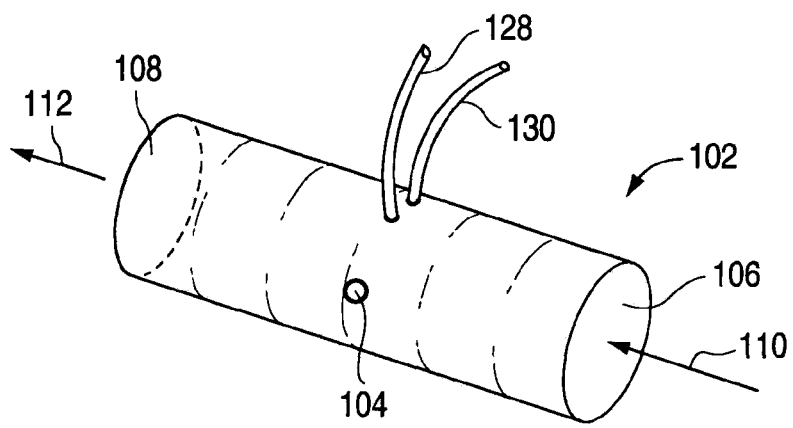
FIG. 2B depicts a three-dimensional view of an embodiment of a chamber of the apparatus of FIG. 2A.

Various embodiments of a method and device for drying a stent in a consistent manner are described herein. FIG. 2A depicts a schematic embodiment of an apparatus 100 for drying a coating material applied to an implantable medical device, such as a stent. Apparatus 100 includes a chamber 102 configured to receive a stent having a coating material applied by a coating apparatus. FIG. 2B depicts a three-dimensional view of an embodiment of chamber 102. As shown, chamber 102 is cylindrically-shaped. However, chamber 102 is not limited to the shape depicted. In other embodiments, chamber 102 may be a conduit with a cross-section including, but not limited to, square, rectangular, oval etc. A coated stent for drying can be inserted into a side opening 104 in chamber 102. Side opening 104 can be positioned, for example, at any location on the surface of chamber 102 adjacent to a desired drying position within chamber 102.

Additionally, chamber 102 has a proximal opening 106 for receiving a stream of heated fluid or gas, as shown by an arrow 110, and a distal opening 108 through which the fluid exits, as shown by an arrow 112. The fluid may be an inert gas such as air, nitrogen, oxygen, argon, etc.

As shown in FIG. 2A, apparatus 100 further includes a heated fluid source 114 that can include a heating element 116 for heating the fluid used for drying a coated stent. For example, fluid source 116 can be a blower with a heating coil. The temperature of the heated fluid may be adjusted by controlling the heat supplied by heating element 116.

Figure 2C:
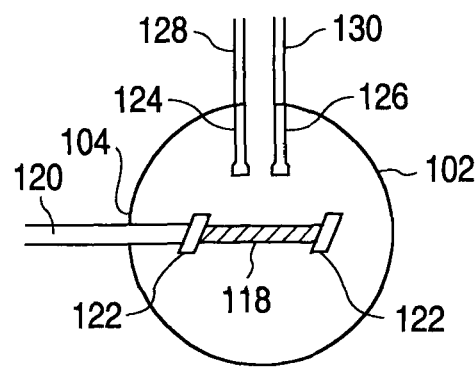
FIG. 2C depicts a radial cross-section of the chamber of FIG. 2B.

FIG. 2C depicts a radial cross-section of chamber 104 along a line A-A in FIG. 2A. A coated stent 118 is shown disposed over a support 120 within chamber 102. Support 120 with stent 118 is disposed through opening 104 and is positioned so that the heated fluid contacts stent 118 to dry the coating. Stent 118 is secured by collets 122 on support 120. Temperature sensors 124 and 126 are positioned adjacent to stent 118 to measure the drying temperature of the applied coating. Temperature sensors 124 and 126 are positioned as close as possible to stent 118 without significantly disrupting the flow of heated fluid past stent 118. In one embodiment, there is no or substantially no offset or difference in temperature between the drying temperature of the coating on the stent and the temperature measured by sensors 124 and 126. In other embodiments, sensors 124 and 126 are positioned far enough away so that there is an offset in the measured temperature and the drying temperature. Such an offset can be taken into account in the control system described below. Temperature sensors 124 and 126 can be thermistors, thermocouples, or any other temperature measuring devices.

Temperature sensor 124 measures the drying temperature to gather feedback ($T_F$) for controlling the drying temperature of stent 118. Sensor 124 is coupled to a control system 132 by a sensor wire 128. Any suitable control system, such as a closed loop system, can be used for maintaining the drying temperature of the coating at a desired temperature ($T_D$). A temperature, $T_F$, measured by sensor 124 is transmitted via wire 128 to control system 132. Control system 132 compares $T_F$ to $T_D$ and then transmits a signal 134 to fluid source 114. Signal 134 carries instructions to fluid source 114 to adjust the temperature of the fluid stream supplied to chamber 102 if the difference in temperature is larger than a selected tolerance. In some embodiments, the desired temperature $T_D$ can be a function of time or thickness.

Temperature sensor 126 monitors a drying temperature of the stent that is independent of a control system. A monitored temperature, $T_M$, can be transmitted by a temperature sensor wire 130 to a display or an automated system (not shown). The control system, in some instances, may be unable to maintain a desired drying temperature. For example, the drying temperature may deviate substantially from a desired temperature. A user can be alerted to the deviation by a displayed $T_M$ and take appropriate action, such as shutting down the drying process and discarding the coated stent. Alternatively, an automated system can be configured to take appropriate action such as shutting down the drying process.

Table 1 presents data for stents dried at two different temperatures using an embodiment of the drying apparatus discussed herein. Ten different sample runs were performed at each temperature. The stents were Xience-V stents obtained from Guidant Corporation, Santa Clara, Calif. The coating runs included application of a primer layer and a drug-matrix or reservoir layer over the primer layer. The coating material for the primer layer was poly(n-butyl methacrylate) (PBMA) in an acetone/cyclohexanone solvent. The coating material for the reservoir layer was poly(vinylidene fluoride-co-hexafluoropropene) copolymer (PVDF-HFP) (e.g., SOLEF 21508, available from Solvay Solexis PVDF, Thorofare, N.J.) in an acetone/cyclohexanone solvent.

Ten samples were dried at each temperature. Each sample was dried over a 24 hour period. Table 1 provides the percentage of solvent released during the drying period for each sample at each temperature.

As expected, a larger percentage of solvent was released at the higher temperature. At 35° C., approximately 72% to 77% of the solvent was released from the stent samples and at 65° C. all or substantially all of the solvent was released. At 65° C., for samples 1, 4, 5, 7, and 9, the measured percentage released was greater than 100%. This is likely due to errors in weighing the stent samples before and after drying. At 35° C., the standard deviation was less than 4° C. and the percent coefficient of variation (% CV) was less than 5° C. At 65° C., the standard deviation and % CV were both less than 2° C. The relatively low values of standard deviation and % CV suggest that the drying method tends to dry stents relatively consistently.

TABLE 1

Percentage of solvent released from coated stent dried at two temperatures over a 24 hour period.

| Sample | Stents Dried at 35° C | Stents Dried at 65° C |
|---|---|---|
| 1 | 72.23 | 101.66 |
| 2 | 74.56 | 97.76 |
| 3 | 74.31 | 97.52 |
| 4 | 72.54 | 101.40 |
| 5 | 72.29 | 102.40 |
| 6 | 73.57 | 98.38 |
| 7 | 76.60 | 101.44 |
| 8 | 63.85 | 97.28 |
| 9 | 75.59 | 100.53 |
| 10 | 74.02 | 98.47 |
| Average | 73.46 | 99.68 |
| Standard Deviation | 3.62 | 1.98 |
| % CV | 4.93 | 1.99 |

Weighing of Stents

The amount of coating material applied to a stent is typically determined by comparing the weight of an uncoated and coated stent. The weight of a coated stent can be taken to be the dry coating weight. Stents are typically weighed using a microbalance, for example, the UMX5 Microbalance from Mettler-Toledo, Inc. of Columbus, Ohio. A sample to be weighed, such as a stent, is disposed on a weighing pan of coupled to a balance for weighing. The maximum capacity of the UMX5 Microbalance including a weighing pan (including its support) is 2.1 g. The weight of a coated stent is approximately 0.4 g. Therefore, the maximum weight of a weighing pan and its support is about 1.7 g for the above-mentioned balance.

Weighing pans that are currently available for microbalances have a maximum surface diameter of under about 28 mm. Therefore, such pans cannot accommodate stents longer than about 28 mm without portions of the stent hanging over an edge of the pan. Hanging portions during weighing are undesirable due to the risk of the stent rolling off the pan. Such pans also have a flat surface with no raised features that facilitate loading of the stent or reduce or prevent rolling off of the stent from the pan.

Figure 3A:
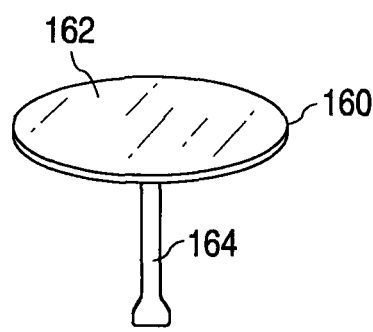
FIGS. 3A-C depict a weighing pan that can accommodate stents under 28 mm in length.
Figure 3B:
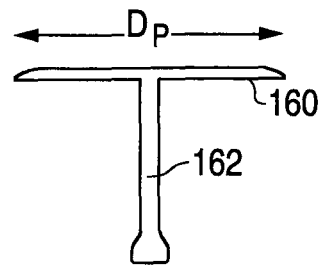
Figure 3C:
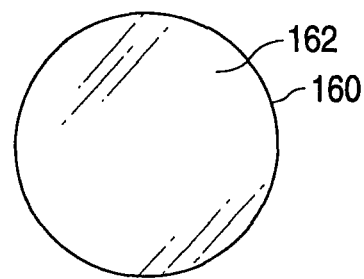

FIGS. 3A-C depict a prior art weighing pan 160 that can accommodate stents under 28 mm in length. Weighing pan 160 is circular with a diameter, $D_P$, of 27.57 mm and has a top surface 162 for supporting a stent. Weighing pan 160 is coupled to a support rod 164 on a bottom surface (not shown). Support rod 164 is configured to be coupled with a balance. Surface 162 of weighing pan 160 is substantially flat and has no features such as indentations or ridges. The weight of weighing pan 160, Mettler Toledo, part number ME-211185, and support rod 164 is approximately 1.2 g.

Stents over 28 mm in length are not accommodated by current weighing pans. However, increasing the diameter of the current weighing pans to accommodate such stents may result in a weighing pan that exceeds the weighing capacity of a typical microbalance. What is needed is a weighing pan that can accommodate stents over 28 mm in length without exceeding the capacity of a typical microbalance.

Embodiments of the present invention relate to a fixture that includes a weighing pan for weighing stents that are greater than about 28 mm in length. In one embodiment, a fixture for supporting a stent during weighing may include a plate or pan. At least a portion of an area of a surface of the pan can support a stent greater than about 28 mm in length along an entire length of the stent without end portions of the stent hanging over an edge of the pan. For example, a portion of an area of the surface can support a 28 mm, 33 mm, or 38 mm stent along its entire length. In certain embodiments, a geometry of the pan is optimized to minimize a mass of the pan, and thus the fixture. In particular, the mass of the fixture may be optimized so that the weight of the fixture and a stent does not exceed the capacity of a selected microbalance.

In one embodiment, the fixture may include a pan having a plurality of holes in a surface of the pan to reduce the mass of the fixture. The pan may have a shape that includes, but is not limited to, circular, oval, rectangular, etc. The holes tend to reduce the mass of the pan while still allowing the surface of the pan to support a stent along its entire length.

Figure 4A:
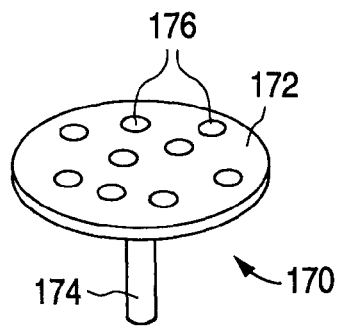
FIG. 4A depicts an embodiment of a weighing pan for a stent.
Figure 4B:
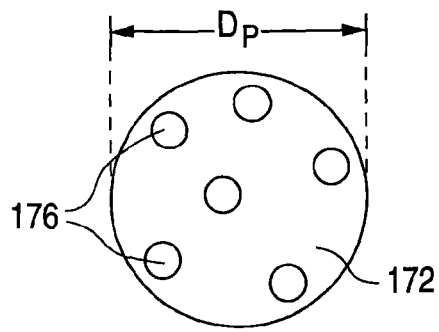
FIG. 4B depicts an overhead view of the pan of FIG. 4A.
Figure 4C:
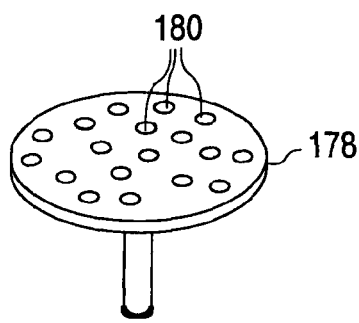
FIG. 4C depicts an embodiment of a weighing pan for a stent.

FIGS. 4A-C depict exemplary embodiments of a fixture for supporting a stent. In FIGS. 4A-B, a fixture 170 has a circular pan 172 and a support rod 174. FIG. 4A depicts a three-dimensional view and FIG. 4B depicts an overhead view of pan 172. Pan 172 includes a plurality of holes 176 which reduce the mass of pan 172 so that the mass of fixture 174 does not exceed the maximum capacity of a microbalance. Pan 172 has a diameter $D_P$ that is large enough to support a stent over 28 mm in length along its entire length. It is desirable for the holes in a pan to be relatively evenly distributed to enhance the stability of the fixture.

The mass of a pan may be optimized to a desired mass by varying the size and number of holes. As the size of the holes decreases, the number of holes required to reduce the mass of the pan a selected amount increases. This is illustrated in FIG. 4C by an exemplary pan 178 with holes 180 which are smaller than holes 176 in pan 172. Pan 178 has a larger number of holes 180 than pan 172 has of holes 176.

Figure 5A:
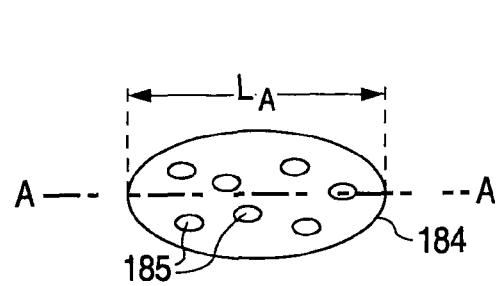
FIGS. 5A-C depict embodiments of weighing pans with asymmetric shapes for stents.
Figure 5B:
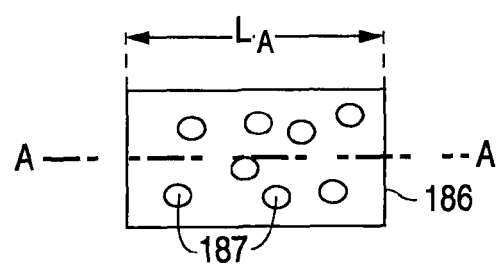
Figure 5C:
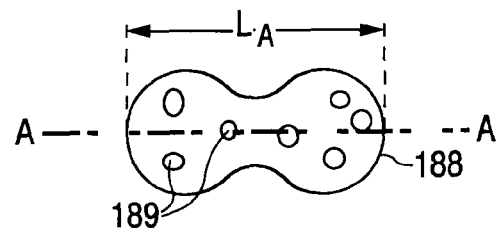

In some embodiments, the pan of a fixture may have an asymmetric shape that is longer along one axis, for example, an oval, rectangular, or dumbbell shape. The surface along the longer axis may be configured to accommodate a stent greater than 28 mm in length along its entire length. FIGS. 5A-C depict exemplary pans with asymmetric shapes which include an oval pan 184, a rectangular pan 186, and a dumbbell-shaped pan 188. An axis A-A corresponds to a longer axis of the shapes in FIGS. 5A-C. A length $L_A$ corresponds to the length along axis A-A. $L_A$ is long enough to support a stent greater than 28 mm. A length along a shorter axis need not be long enough to support the stent. Pans 184, 186, and 188 can include holes 185, 187, and 189, respectively, to further optimize the mass of the pan.

Figure 6A:
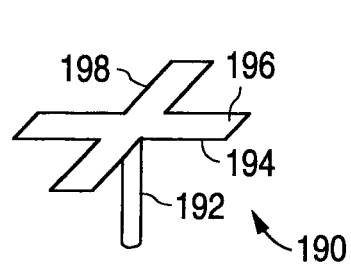
FIG. 6A depicts an embodiment of a cross-shaped weighing pan for a stent.
Figure 6B:
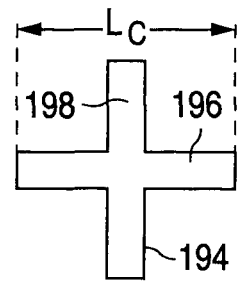
FIG. 6B depicts an overhead view of the pan of FIG. 6A.
Figure 6C:
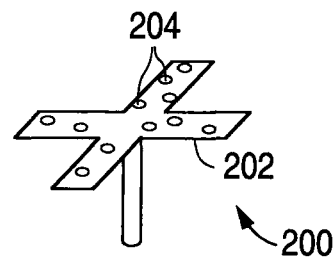
FIG. 6C depicts an embodiment of a cross-shaped weighing pan for a stent.

As the asymmetry of a pan increases, a fixture may tend to become less stable. Additionally, a stent has an increased risk of rolling off a pan that is highly asymmetric. A more stable geometry of the pan may include at least two intersecting elongated portions. At least one of the intersecting portions may be adapted to support a stent greater 28 mm in length along its entire length. FIGS. 6A-B depict a fixture 190 with a cross-shaped pan 194 supported by a support rod 192. Cross-shaped pan 194 includes intersecting rectangular portions 196 and 198. A length $L_C$ of rectangular portion 196 is long enough to support a stent longer than about 28 mm along its entire length. The mass of the cross-shaped pan can further be optimized with holes. FIG. 6C depicts a fixture 200 with a cross-shaped pan 202 with holes 204.

Figure 7:
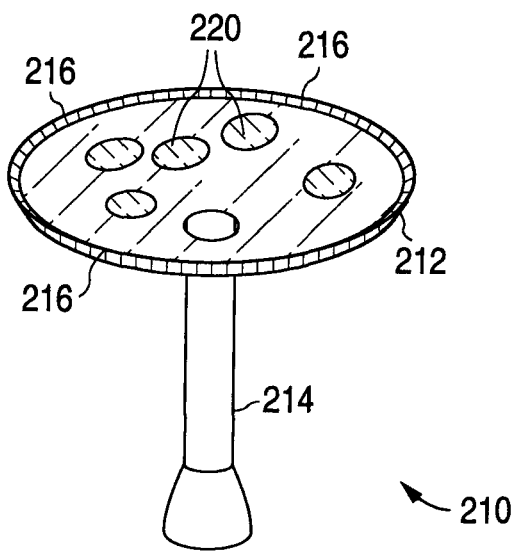
FIG. 7 depicts an embodiment of a weighing pan with a ridge around its edge.

In some embodiments, a weighing pan may include surface features at or adjacent to at least a portion of an edge of the pan to facilitate placement or removal of a stent on the pan. The features may also inhibit a stent from falling or rolling off the pan. For example, the features may include, but are not limited to, ridges, bumps, or protrusions along at least a portion of the pan. FIG. 7 depicts a fixture 210 including a pan 212 with holes 220 supported by a support member 214. Pan 212 includes a ridge 216 extending all the way around the edge of pan 212. Ridge 216 can also be discontinuous, i.e., ridge 212 can include a series of discrete portions separated by gaps.

Improving Throughput of Coating Process

A further aspect of the present invention relates to manipulation of spray coating parameters to obtain desired processing goals and coating characteristics. Spray coating parameters that may be manipulated can include, but are not limited to, flow rate of coating material, axial translation speed of stent, rotation speed, nozzle height, and atomization pressure.

Figure 8:
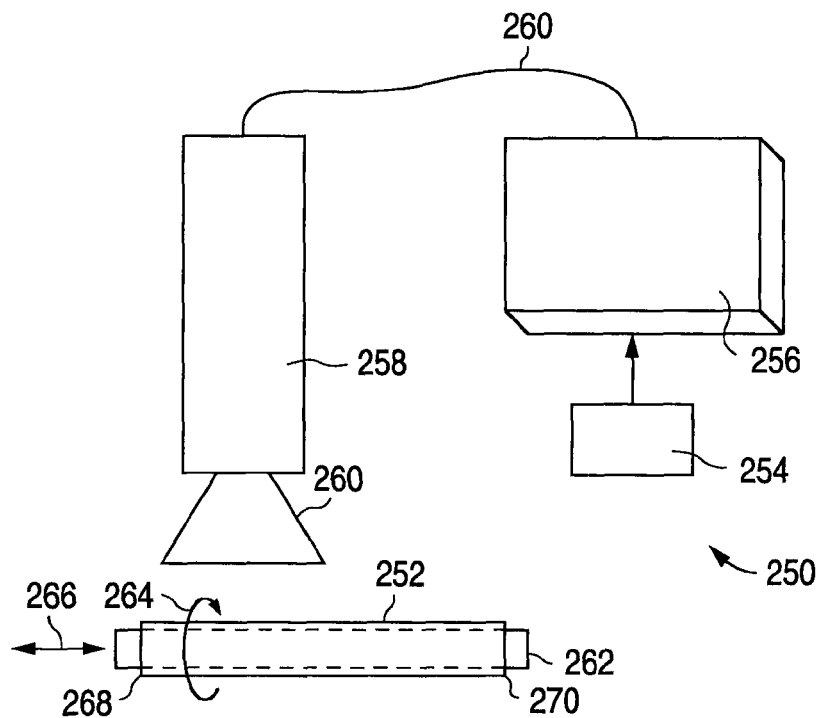
FIG. 8 depicts an exemplary schematic embodiment of a spray coating apparatus for coating a stent.

FIG. 8 depicts an exemplary schematic embodiment of a spray coating apparatus 250 for coating a stent 252. A syringe pump 256 pumps coating material from a reservoir 254 that is in fluid communication with a spray nozzle 258. Nozzle 258 can be in fluid communication with pump 256 through a hose 260. Nozzle 258 provides a plume 260 of coating material for depositing on stent 252. A flow rate of coating material provided by nozzle 258 can be varied by changing the pump rate of pump 256.

Stent 252 is supported by a stent support 262, such as a mandrel, other support devices known in the art, or support devices as described herein. Support 262 is configured to rotate stent 252 about its cylindrical axis, as shown by an arrow 264. Support 262 is also configured to axially or linearly translate stent 252 with respect to plume 260, as shown by an arrow 266. In other embodiments, nozzle 258 can be translated along the cylindrical axis of stent 252 rather than or in addition to axially translating stent 252.

Coating material is deposited on stent 252 as it is translated through plume 260 from a proximal end 268 to a distal end 270 of stent 252. After a selected number of passes through plume 260, the deposited coating material is allowed to dry or subjected to a drying process known in the art or described herein prior to further deposition of coating material. The deposition and drying steps are repeated until a desired amount of coating material is deposited on stent 252.

One aspect of the present invention relates to increasing the rate of the coating process or increasing throughput of the coated stents while maintaining coating quality. In one embodiment, the rate of the coating process can be increased by increasing the flow rate of coating material through nozzle. This can be accomplished by increasing the pump rate of coating material, as described above. An increased flow rate of coating material increases the amount or mass of coating material deposited per unit time on the stent or per pass of the nozzle over the stent.

However, increasing the flow rate, and mass per pass, can have deleterious effects on coating quality. First, an increased mass per pass can lead to defects in the coating, as well as inconsistencies in the coating from layer to layer and stent to stent. Second, increasing the mass per mass increases the drying time of the deposited coating material. Due to the increased drying time, there is an increased likelihood of the nozzle clogging between passes. Residual coating material in the nozzle can dry and reduce or prevent flow of coating material through the nozzle. Embodiments of the method described herein allow an increase in throughput and flow rate of coating material while maintaining coating consistency resulting in an acceptable level of defects. In addition, the increased flow rate does not lead to an increase in nozzle clogging.

Certain embodiments of a method of coating a stent may include modifying a flow rate of coating material sprayed onto a stent by a coating apparatus. The method may further include adjusting an axial translation speed of the stent based on the modified flow rate during spraying of the coating material to obtain a selected amount of deposition of coating material per pass of the stent relative to the nozzle. In one embodiment, an axial translation speed of the stent may be controlled to obtain a selected amount of deposition or mass per pass of coating material.

In an embodiment, the flow rate of the coating material directed at the stent from a nozzle of the coating apparatus may be increased. The axial translation speed may then be increased to compensate for the increased flow rate. The increased axial translation speed tends to decrease the mass per pass at the increased flow rate. The axial translation speed may be increased so that the mass per pass does not result in a drying time that results in clogging of the nozzle during drying of deposited coating material on the stent. In addition, the axial translation speed may be increased so that the mass per pass results in a relatively consistent coating from pass to pass and that has an acceptable quantity and degree of defects.

Table 2 illustrates the effect of pump rate and linear or axial speed on the mass per pass and coating quality. The coating quality was based on a visual inspection of the coated stent under a microscope. Inspections are performed of a coated stent at a magnification between 40× and 100× under a microscope. The coating quality is based on size and number of defects including the presence of cobwebs and rough spots. In general, in order to pass, a stent must be free of defects over a certain size and have less than a specified number of cobwebs and rough spots.

Coating runs were performed on a 28 mm stent for different pump rates of coating material and linear or axial speed of the stent under a nozzle. The mass per mass in each run was determined by the difference in weight of the stent before and after coating.

The coating runs included application of a primer layer and a drug-matrix or reservoir layer over the primer layer. The coating material for the primer layer was poly(n-butyl methacrylate) (PBMA) in an acetone/cyclohexanone solvent. The coating material for the reservoir layer was poly(vinylidene fluoride-co-hexafluoropropene) copolymer (PVDF-HFP) (e.g., SOLEF 21508, available from Solvay Solexis PVDF, Thorofare, N.J.) in an acetone/cyclohexanone solvent.

The coating equipment included a Havard syringe pump obtained from Instech Laboratories, Inc., Plymouth Meeting, Pa. The nozzle and mandrel used were developed in-house.

As shown in Table 2, Runs 1 and 2 were performed at a pump rate of 12 mg/sec and linear or axial speed of 6 mm/sec. The mass per pass differed slightly between the two runs and the coating quality was a "pass."

The linear or axial speed for Runs 3-6 was increased from 6 mm/sec to 12 mm/sec from Runs 1 and 2. The pump rate for Runs 3-6 was the same as Runs 1 and 2. Table 2 shows, as expected, that the increase in the linear or axial speed caused a decrease in the mass per mass. As indicated above, an increase in linear or axial speed tends to decrease the mass per pass. The mass per pass of Runs 3-6 is slightly more than a third of the mass per pass of Runs 1 and 2. In addition, the coating quality was a "pass" for each of Runs 3-6.

In Runs 7-10, both the pump rate and linear or axial speed were increased over that used in Runs 3-6 from 12 ml/hr to 18 ml/hr and 12 mm/sec to 18 mm/sec, respectively. In general, the increase in the pump rate tends to increase the mass per pass. However, the increase in the linear or axial speed compensates for the increase in the increased pump rate since the mass per pass of Runs 7-10 is less than Runs 3-6. The coating quality is a "pass" for Runs 8-10 and a "fail" for Run 7.

In Runs 11 and 12, the pump rate and linear or axial speed were both further increased over that used in Runs 7-10 from 18 ml/hr to 24 ml/hr and from 18 mm/sec to 24 mm/sec, respectively. In this case, the increase in the pump rate resulted in an increase in the mass per pass. The increase in the linear or axial speed only partially compensated for the increase in flow rate. In each of Runs 11 and 12, the coating quality was a pass. Nominal refers to the center or standard parameter run.

TABLE 2

Test coating runs for different pump rates and linear or axial speed.

| Test | Mass Per Pass (µg/pass) | Pump Rate (ml/hr) | Axial Speed (mm/sec) | Visual Inspection |
|---|---|---|---|---|
| Test Conditions for 28 mm Stent | | | | |
| 1 | 92 | 12 | 6 | Pass |
| 2 | 95 | 12 | 6 | Pass |
| 3 | 35 | 12 | 12 | Pass |
| 4 | 34 | 12 | 12 | Pass |
| 5 | 36 | 12 | 12 | Pass |
| 6 | 36 | 12 | 12 | Pass |
| 7 | 24 | 18 | 18 | Fail |
| 8 | 23 | 18 | 18 | Pass |
| 9 | 23 | 18 | 18 | Pass |
| 10 | 19 | 18 | 18 | Pass |
| 11 | 38 | 24 | 24 | Pass |
| 12 | 32 | 24 | 24 | Pass |
| Nominal Conditions for 28 mm Stent | | | | |
| 13 | 30 | 5 | 6 | |

Stent Support Assemblies

Another aspect of the present invention relates to reducing or eliminating coating defects that can result from stent contact with supports, such as mandrels, during coating. A shortcoming of the above-described method of medicating a stent through application of a coating is the potential for coating defects. While some coating defects can be minimized by adjusting the coating parameters, other defects occur due to the nature of the interface between the stent and the apparatus on which the stent is supported during the coating process. A high degree of surface contact between the stent and the supporting apparatus can provide regions in which the liquid composition can flow, wick, and collect as the composition is applied. As the solvent evaporates, the excess composition hardens to form excess coating at and around the contact points between the stent and the supporting apparatus. Upon the removal of the coated stent from the supporting apparatus, the excess coating may stick to the apparatus, thereby removing some of the needed coating from the stent and leaving bare areas. Alternatively, the excess coating may stick to the stent, thereby leaving excess coating as clumps or pools on the struts or webbing between the struts.

Thus, it is desirable to minimize the influence of the interface between the stent and the supporting apparatus during the coating process to reduce or coating defects. Accordingly, the present invention provides for embodiments of a method and device for supporting a stent during the coating application process that minimizes the influence of the interface.

As described above, spray coating a stent typically involves mounting or disposing a stent on a support, followed by spraying a coating material from a nozzle onto the mounted stent. A stent can be supported, for example, on a mandrel or rod that supports the stent along its length by positioning the stent over the mandrel. A stent can also be supported at its ends with supports having a variety of geometries, such as tapered or untapered cylinders.

As indicated above, the interface or contact points between a stent support and the stent can lead to defects. This is particularly the case where the support and the stent do not move relative to one another during the coating process. The lack of relative movement leads to stationary contact points between the stent and the support.

The contact area between a support and stent can be minimized by sizing a support such as a mandrel so that its diameter is less than the inside diameter of the stent. Similarly, the ends of a stent can be supported loosely over tapered or untapered cylinders. Thus, as the mandrel rotates, the contact points continuously change. A disadvantage of this approach is that the stent can stick to the support members, resulting in stationary contact points.

Embodiments of the present invention relate to a method of and a device for shifting or changing the contact points of a stent with a support during a coating process. In certain embodiments, the shift in contact points may be accomplished by a pulse in the rotation rate of a support member that rotates and causes a stent to rotate. A "pulse" generally refers to a rise and/or fall in a quantity during a period of time. Shifting or changing a contact point, area, or interface refers to a change of a point, area, or interface of contact of a stent with a support from one location of the support to another location of the support.

Figure 9:
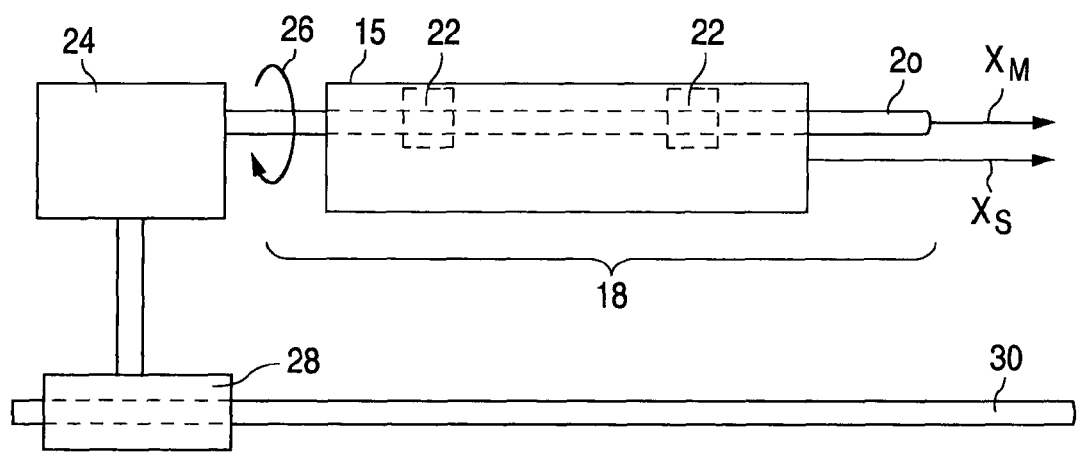
FIG. 9 depicts a mounting assembly for supporting a stent.

FIG. 9 depicts a mounting assembly 18 for supporting a stent 15 including a rod or mandrel 20 and support elements 22. Mandrel 20 can connect to a motor 24, which provides rotational motion to mandrel 20, as depicted by an arrow 26, during the coating process. Motor 24 is also capable of providing rotational pulses for shifting contact points, as described below. Another motor 28 can also be provided for moving mandrel 20 and thus stent 15 in a linear or axial direction, back and forth, along a rail 30. Motor 28 is also capable of providing translational pulses to mandrel 20 along its axis. Pulsing motors include an electronic gearing system that can cause a pulse or change in the rotation rate or cause a pulse in the axial translation of a support element.

Mandrel 20 is illustrated as having two regions with a larger diameter. The two regions can be support elements 22 for applying a torque to stent 15. In commercially useful embodiments, any number of support elements 22 can be used to adequately support stent 15. As shown, support elements 22 are sized larger than the outer diameter of mandrel 20 so as to prevent mandrel 20 from being in contact with the inner surface of stent 15. Alternatively, in other embodiments, mandrel 20 can be free of support elements 22 so that the stent is supported by and in contact with mandrel 20.

Additionally, support elements 22 are sized smaller than the inner diameter of stent 15 so as to provide for minimum contact between support elements 22 and the inner surface of stent 15. In the case of a mandrel 20 free of support elements 22, mandrel 22 is sized smaller than the inner diameter of stent 15.

Support elements 22 of small diameter, as compared to the inner diameter of stent 10, results in an axis $x_M$ about which support elements 22 rotate, that is offset from an axis $x_S$, about which stent 15 rotates. Axis $x_S$ is positioned longitudinally through the center of stent 15. Since support elements 22 and stent 15 rotate about different axes, $x_M$ and $x_S$, support elements 22 and stent 15 do not have a 1:1 rotation. Thus, the contact points or area between support 22 and stent 15 continuously change. However, coating material can cause stent 15 to stick to support elements 22, resulting in a stationary contact point.

Sticking of stent 15 to support elements 22 is reduced or prevented by pulsing the rotation rate of mandrel 20 and elements 22. The pulses in rotation rate cause a stent that is stuck to one or both of support elements 22 to break free and resume rotation about axis $x_S$ with continuously changing contact points.

Numerous variations of the form of a pulse that could break a stent free are possible. FIGS. 10A-D each depict the rotation rate as a function of time for representative pulses. The pulse duration can be, for example, between 0.0001 sec and 1 sec. A pulse duration outside this range can be contemplated by one of skill in the art. $R_1$ is the rate prior to the pulse, $R_2$ is the maximum rate of the pulse, and $R_3$ is a final rate of the pulse (in FIGS. 10A-C). $R_1$ can also correspond to the rotation rate of the opposing non-pulsing element. FIGS. 10A-D depict pulses that have an increase in rotation rate. However, pulses with a decrease in rotation rate can also be used to reduce or prevent sticking, as well as shifting contact points, as described below.

Figure 10A:
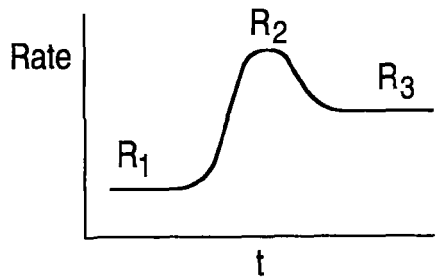
FIGS. 10A-D depict the rotation rate as a function of time for representative pulses in rotation rate.
Figure 10B:
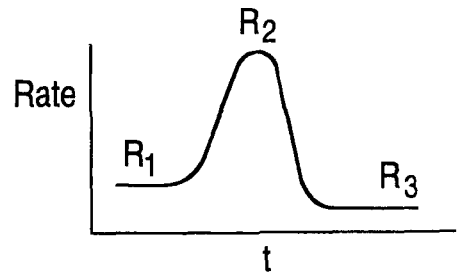
Figure 10C:
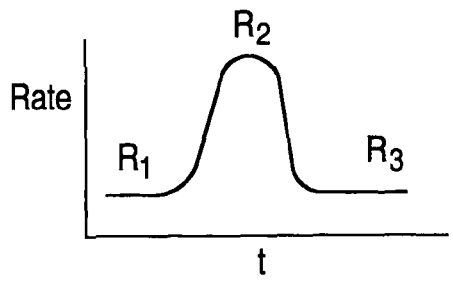
Figure 10D:
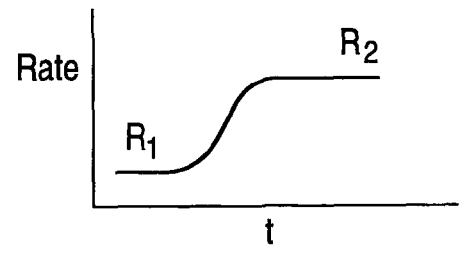

In FIGS. 10A-C, the rotation rate increases from $R_1$ to a peak at $R_2$ and then decreases to $R_3$. $R_3$ is greater than $R_1$ in FIG. 10A, less than $R_1$ in FIG. 10B, and the same as $R_1$ in FIG. 10C. The maximum rate, $R_2$ of the pulse can be greater than 10%, 30%, 60%, 80%, or more narrowly greater than 100% of the rate prior to the pulse, $R_1$.

The pulses can be performed at a specified frequency during the coating process to reduce or eliminate sticking of the stent that can occur. The frequency can be greater than 0.1 Hz, 0.5 Hz, 1 Hz, 3 Hz, or more narrowly 5 Hz. Alternatively, the pulses can be performed at irregular or unequal intervals.

A pulse causes a rotation of elements 22 relative to stent 15. The relative rotation caused by an increase in rate from $R_1$ to $R_2$ can be greater than 10°, 30°, 45°, 90°, or 270°. The amount of rotation can be controlled by the maximum rate of the pulse, the degree of acceleration, and the duration of the pulse. It is believed that the higher rate $R_2$ or degree of acceleration, the greater is the relative rotation of elements 22 to stent 15.

Figure 11A:
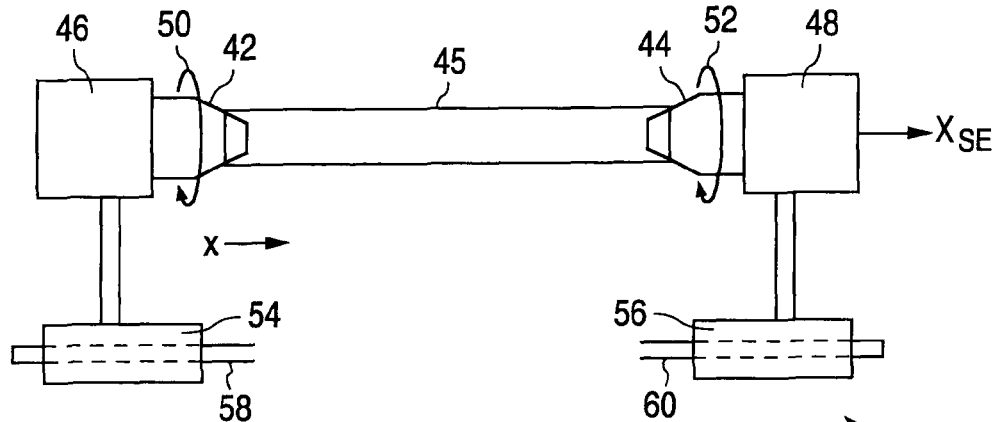
FIGS. 11A-B depict mounting assemblies for supporting a stent.

FIG. 11A depicts a mounting assembly 40 which supports stent 45 via support elements 42 and 44. Support elements 42 and 44 have a cylindrical cross-section and taper inwardly toward stent 45. As shown, the ends of stent 45 can rest on the tapered portions of support elements 42 and 44. A variety of shapes can be contemplated by one of ordinary skill in the art for support elements 42 and 44.

Support elements 42 and 44 can connect to motors 46 and 48, respectively, which provide rotational motion to support elements 42 and 44, as depicted by arrows 50 and 52, during the coating process. Motors 46 and 48 are also capable of providing rotational pulses for shifting contact points, as described below. Motors 54 and 56 can also be provided for providing pulses to support elements 42 and 44 in a linear direction along rails 58 and 60, respectively. Motors 54 and 56 are also used to position support elements 42 and 44 relative to one another. Another motor (not shown) can also be provided to move assembly 40 and thus stent 45 in a linear direction, back and forth, during coating.

Support elements 42 and 44 can be positioned by motors 54 and 56, respectively, so that support elements 42 and 44 and stent 45 have the same or substantially the same axes of rotation. Opposing forces exerted from support elements 42 and 44, for securely pinching stent 45 against support elements 42 and 44, should be sufficiently strong so as to prevent any significant movement of stent 45 on mounting assembly 40. The forces can be sufficiently strong so that there is a 1:1 rotation of stent 45 with support elements 42 and 44.

However, the exerted force should not compress stent 45 so as to distort the body of stent 45. Over or under application of support force can lead to problems such as stent 45 resting too loosely on mounting assembly 20, stent 45 bending, opposing ends of stent 45 flaring on support elements 42 and 44, and increased contact between stent 10 and support elements 42 and 44, all of which can lead to coating defects.

Additionally, stent 45 can be disposed loose enough on support elements 42 or 44 so that there is not 1:1 rotation between stent 45 and support elements 42 or 44. Support elements 42 and 44 can be positioned relative to one another so that stent 45 has an axis of rotation different from an axis of rotation of the support elements. In this case, the contact points or area between support elements 42 and 44 and stent 10 continuously change.

When there is 1:1 rotation between a support element and the stent, contact points between the support and the stent tend not to change if the rotation rate of elements 42 and 44 are the same. As discussed above, contact points that do not change for all or a substantial part of the coating process can lead to coating defects. A shift in contact points during coating can reduce or eliminate defects due to contact points during coating. Providing a rotational pulse to a support element can shift the contact points between the support element and the stent. Contact points that are uncovered due to a shift may then be covered by coating material. A repeated shifting of contact points during coating tends to allow coating material to cover defects or uncoated regions caused by contact points during the coating process.

Motor 46 can rotate support element 42 at the same or different rate as motor 48 rotates support element 44. Thus, motor 46 and motor 48 can provide rotational pulses independent of one another to support elements 42 and 44, respectively, to shift contact points between stent 45 and support elements 42 and 44. The pulses can take the form of those shown in FIGS. 10A-D. As discussed above, a rotational pulse causes a rotation of support elements 42 or 44 relative to stent 45. An increase in rotation rate of element 42 from $R_1$ to $R_2$ causes element 42 to rotate ahead of stent 302 resulting in a shift of contact points between stent 45 and element 42. The relative rotation can continue as long the rotation rate of element 42 differs from element 44. However, if both ends of the stent are stuck, coupled, or attached to the respective collets resulting in 1:1 rotation at each end, a difference in velocity between the ends could damage or destroy the stent. The stent could be twisted and damaged or destroyed by a torsional force.

The pulses can be performed at a specified frequency during the coating to reduce or eliminate the defects caused by contact points. A pulse rotates elements 42 or 44 relative to stent 45 resulting in different contact points after the pulse. As above, the relative rotation can be greater than 10°, 30°, 45°, 90°, or 270°. The degree of rotation can be controlled by the maximum rate of the pulse, the degree of acceleration, and the duration of the pulse.

When stent 45 is loosely supported on support elements 42 and 44 so that there is not a 1:1 rotation, rotational pulses can reduce or prevent sticking of stent 45 to support elements 42. Sticking can also be reduced or prevented by rotating support elements 42 and 44 at different rates. Rotating support elements 42 and 44 at different rates can reduce or prevent sticking of the ends of stent 10 to elements 42 or 44. The difference in torque at the different ends of stent 10 causes the slower end to pull back on the faster end and the faster end to pull forward on the slower end to reduce or prevent sticking or to break free an end that is sticking. The difference in torque between elements 42 and 44 should be small enough so as not to cause excessive flexure to the stent.

Contact points between stent 45 and support elements 42 and 44 can be shifted by pulsing support elements 42 and 44 in a linear direction. Sticking of stent 45 to support elements 42 or 44 can also be reduced or prevented by linear pulses. Motor 54 or motor 56 can provide linear pulses independent of one another to support elements 42 and 44, respectively. A linear pulse involves an axial translation of support elements 42 or 44 by motors 54 or 56, respectively.

Figure 12:
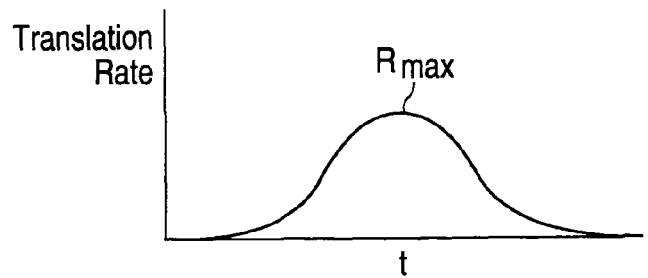
FIG. 12 depicts a representative linear pulse showing linear translation rate versus time.

Motors 54 or 56 can pulse support elements 42 or 44, respectively, either inward toward stent 45 or outward away from stent 45. A representative linear pulse showing linear translation rate versus time is depicted in FIG. 12. The rate corresponds to the linear translation rate of support element 42 or 44 relative to the assembly 40 which can be translated back a forth during coating. In FIG. 12, the translation rate increases from zero to $R_{max}$ and then returns to zero. For example, support element 42 can be pulsed inward toward stent 45 with a pulse having the functional form in FIG. 12. Support element 42 can be pulsed outward in a similar manner.

Figure 13A:
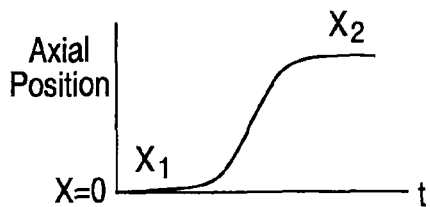
FIGS. 13A-H depict the axial position of a support element as a function of time.
Figure 13B:
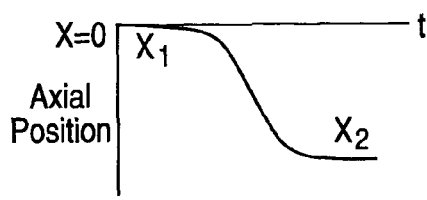
Figure 13C:
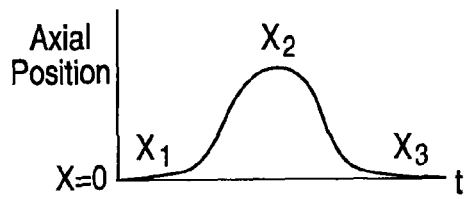
Figure 13D:
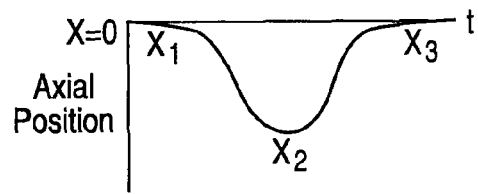
Figure 13E:
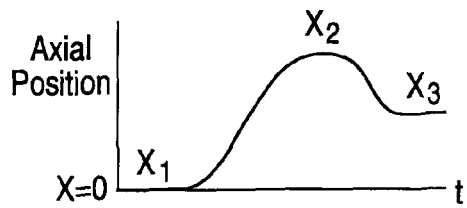
Figure 13F:
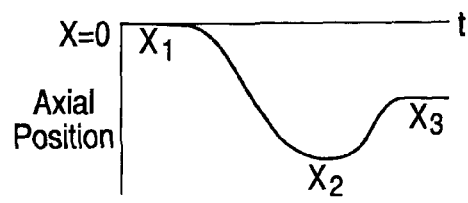
Figure 13G:
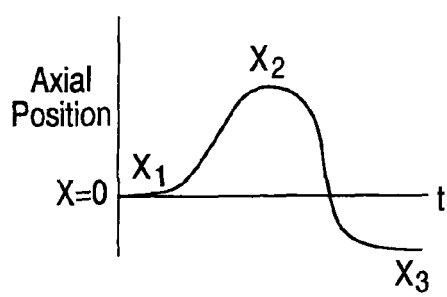
Figure 13H:
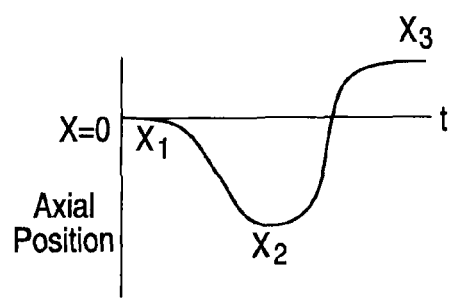

Pulses or a suitable combination of pulses can cause axial translation of supports 42 and 44 with respect to stent 45 in a number of ways. FIGS. 13A-H show the axial position of an end of support element 42 or 44 as a function of time. "$x_1$" is the initial position of a point on a support element, "$x_2$" is the maximum linear deviation from the initial position. "$x_3$" is the final position of the support element in FIGS. 13C-H. FIGS. 13A-B depict movement of a support element from a position $x_1$ to a position $x_2$. For example, for support element 42, FIG. 13A depicts a movement inward and 13B is a movement outward from the stent. FIGS. 13C-D depict a movement of a support element from a position $x_1$ to a position $x_2$ followed by a movement back to $x_1$. FIGS. 13E-F depict a movement of a support element from a position $x_1$ to a position $x_2$ followed by a movement to a position between $x_1$ and $x_2$. FIGS. 13G-H depict a movement from of a support element from a position $x_1$ to a position $x_2$ followed by a movement to a position that is further from $x_2$ than $x_1$.

The linear pulses tend to reduce or prevent sticking of the stent to support element 42 or 44. When support element 42 or 44 is translated inward toward the stent, the stent tends to slide or ride upward along the upper tapered portion of support element 42 or 43. Similarly, when support element 42 or 44 is translated outward away from the stent, the stent tends to slide or ride downward along the upper tapered portion of support element 42 or 44.

Figure 11B:
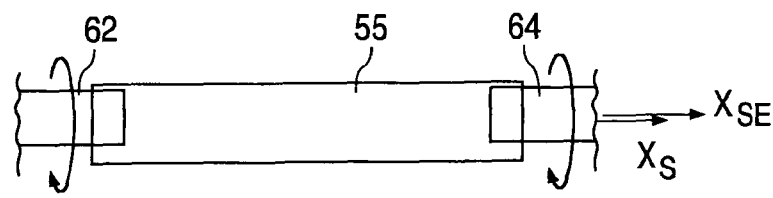

FIG. 11B depicts a part of a mounting assembly with support elements 62 and 64 supporting stent 55. Support elements 62 and 64 are untapered cylindrical elements. Support elements 62 and 64 can be sized so that there is a 1:1 rotation between stent 55 and the support elements. Rotational and linear pulses can be used to shift contact points between support elements 62 and 64 and stent 55. Support elements 62 and 64 can be sized smaller than the inner diameter of stent 55 so that the support elements and stent 55 have a different axis of rotation. Sticking of stent 55 to support elements 62 and 64 can be reduced or prevented by rotational and linear pulses.

In further embodiments, assembly 40 can include only one rotatable support element, e.g., support element 42, with the opposing support element being rotationally fixed. An end of stent 45 can fit loosely over an opposing support element so that there is not a 1:1 rotation of stent 45 with the support element. Such a support element can have a variety of shapes including those pictured in FIGS. 11A-B.

Figure 14A:
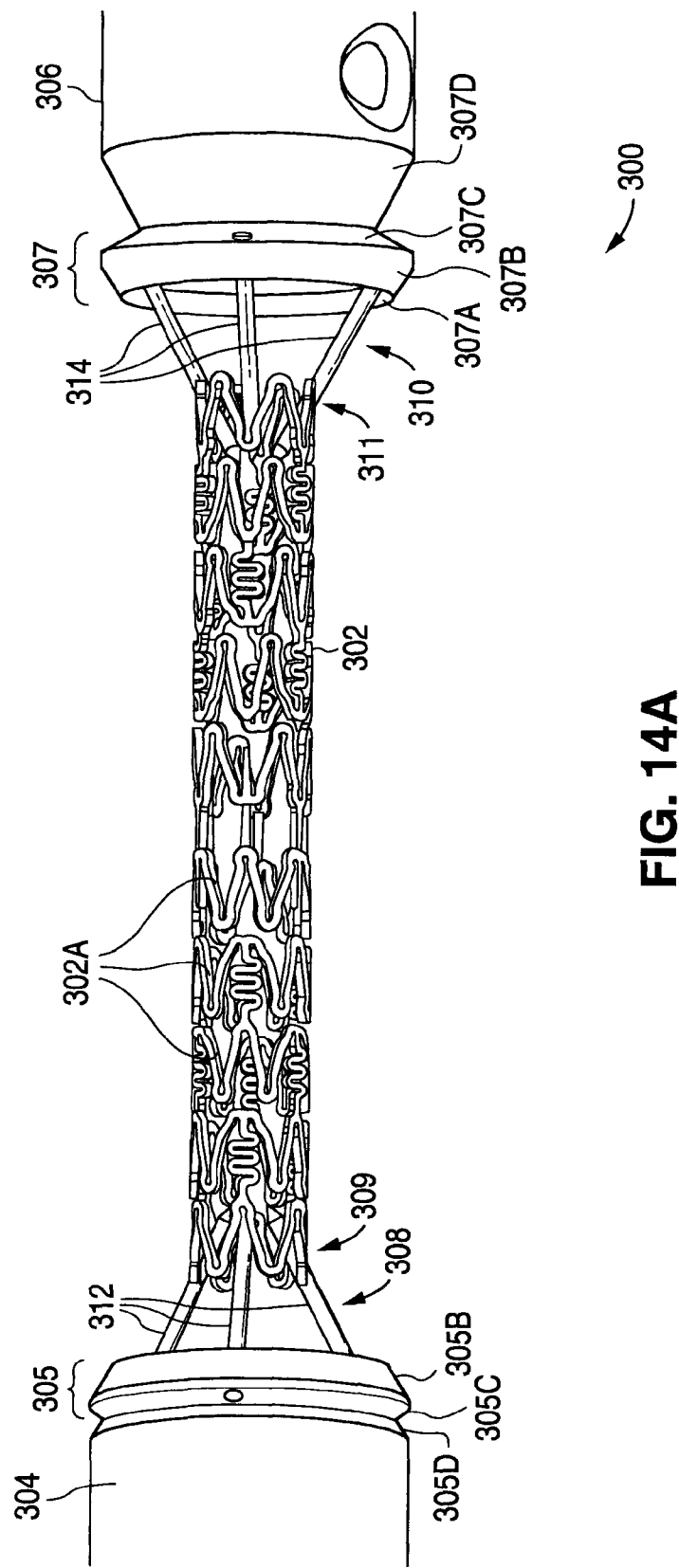
FIG. 14A depicts an embodiment of a stent support system.
Figure 14B:
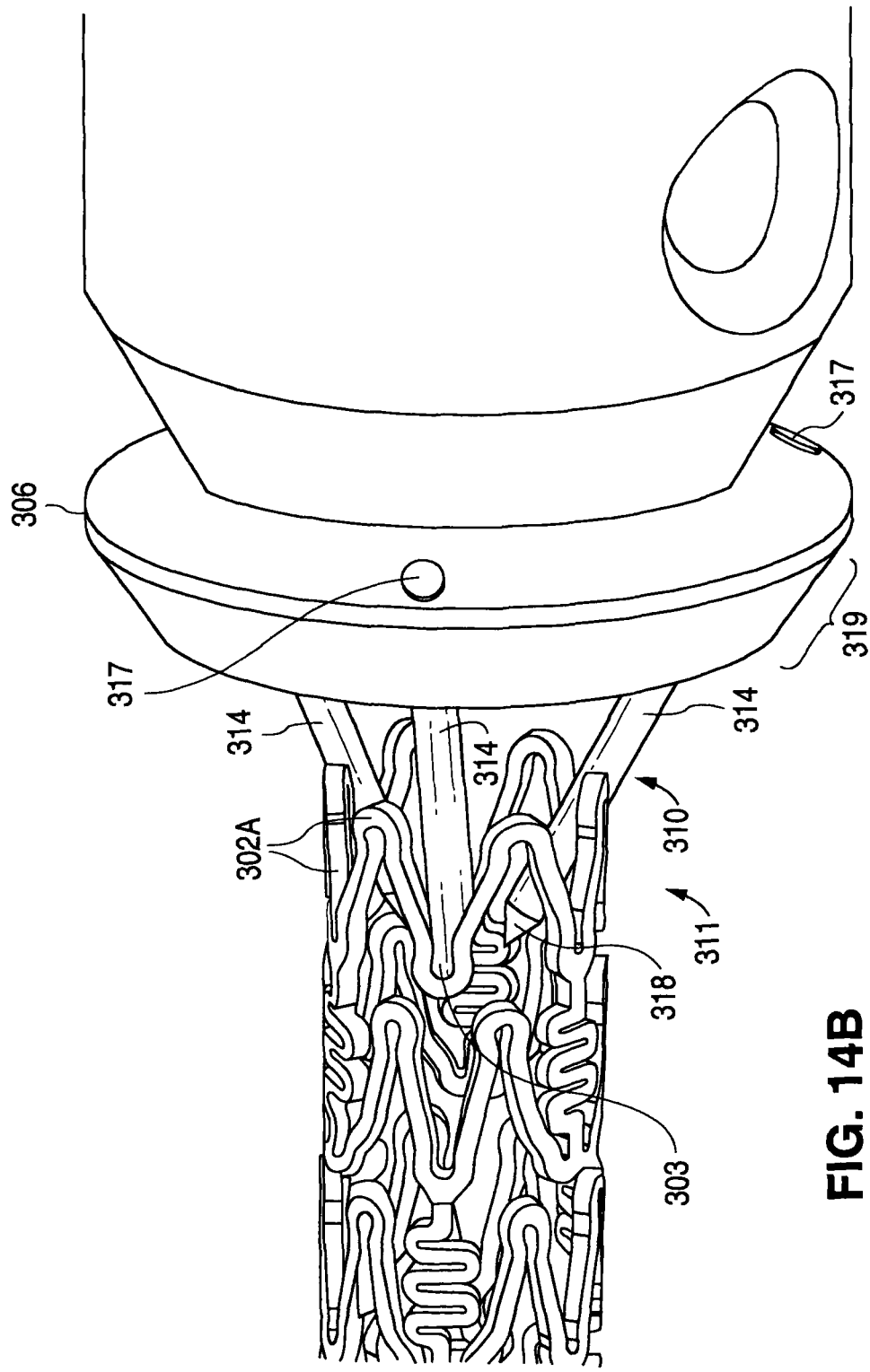
FIG. 14B depicts a close-up view of one side of the stent support system of FIG. 14A.

FIGS. 14A-B depict an additional exemplary embodiment of a stent support assembly 300 that provides for changing or shifting of contact points of a stent 302 with a stent support. Stent 302 has a geometry composed of a plurality of undulating and intersecting elements or struts 302A. Assembly 300 includes a rotary spindle 304 and a rotary spindle 306 that can rotate independently of one another.

A support element 308 and a support element 310 are coupled to rotary spindle 304 and rotary spindle 306, respectively. Rotary spindles 304 and 306 can rotate support elements 308 and 310, and thus, stent 302 supported by elements 308 and 310. Support element 308 supports a proximal end 309 of stent 302 and support 310 supports a distal end 311 of stent 302. Rotary spindles 304 and 306 are each connected to motors (not shown) which provide rotational motion to support elements 308 and 310 and to stent 302. The rotational motors are also capable of providing rotational pulses, as described above. Additionally, rotary spindles 304 and 306 are also connected to linear motors (not shown) for positioning support elements 308 and 310 relative to one another and for providing translational pulses to support elements 308 and 310 in a linear or axial direction. Another motor (not shown) can also be provided to move an assembly including spindles 304 and 306, and thus, stent 302 in a linear direction, back and forth, during coating.

Support element 308 includes three elongate arms 312 coupled to spindle 304 and support element 310 also includes three elongate arms 314 coupled to spindle 306. Elongate arms 312 and 314 converge inwardly to form a conical or frusto-conical shape for supporting stent 302. As depicted in FIG. 14B, elements 312 and 314 have cylindrical cross-sections and have pointed ends 318 that taper to a thin tip. Elements 312 and 314 can have other cross-sectional shapes such as triangular, square, rectangular, etc. Also, ends 318 can be flat or rounded. Elongate arms 312 and 314 may be, for example, wires or rods.

The ends of spindles 304 and 306 each have projecting portions 305 and 307. Portion 307 has an inner edge 307A, an edge 307B that tapers inward toward stent 302 to meet edge 307A, an edge 307C that tapers outward toward stent 302 to meet edge 307B. An edge 307D tapers inward toward stent 302 to meet edge 307C. Spindle 304 has corresponding elements including edge 305B, edge 305C, and edge 305D. Edge 307D has a longer a more gradual taper than edge 305D.

As shown in FIG. 14B, elongate arms 312 and 314 are coupled to rotation spindles 304 and 306. Edges 307A and 307C have holes sized to receive elements 314. Elements 314 are disposed through the holes to couple elements 314 to portion 307. Elements 312 are similarly coupled to or disposed in portion 305. Elongate arms 312 and 314 can be, for example, screwed, glued, riveted, or friction-fitted into the holes.

Elongate arms 312 and 314 extend into and support a proximal end 309 and a distal end 311, respectively of stent 302. Each of elongate arms 312 and 314 have at least one point or area of contact with struts 302A at proximal end 309 and distal end 311, respectively. Elongate arms 312 and 314 are sized to be capable of supporting the stent, for example, so that an elongate arm can support stent 302 without passing through a narrow portion 303 of the stent pattern. Support elements 308 and 310 are positioned within ends 309 and 311 by translating the support elements with respect to each other using the linear motors mentioned above.

In one embodiment, elongate elements 312 and 314 can be rigid such that the elements exhibit no or relatively no bending while being positioned within a stent or during coating. Alternatively, elongate elements 312 or 314 can be flexible. As flexible elements 312 or 314 are positioned into an end of stent 302, the flexible elements bend inward and can exhibit an outward radial force that facilitates securing the elongate elements to stent 302.

Stent 302 can be rotated during coating by rotating rotary spindles 304 and 306 which rotate support elements 308 and 310, and thus, stent 302. Elements 308 and 310 can be positioned within ends 309 and 311 so that there is 1:1 rotation between elements 308 and 310 and stent 302. As described for elements 42 and 44 in FIG. 11A, the relative distance between elements 308 and 310 can be decreased so that elongate elements 312 and 314 securely pinch ends 309 and 311 of stent 302. The opposing forces exerted from support elements 308 and 310 should be sufficiently strong so as to prevent any significant movement of stent 302. However, the exerted force should not compress stent 302 so as to distort the body of stent 302. When support elements 308 and 310 rotate at the same rate or rotate in phase, the contact points between elements 308 and 310 with stent 302 tend to remain the same, as described for elements 42 or 44 in FIG. 11A.

Providing a rotational pulse to, for example, element 308 causes a shift or change in the contact points between each of elements 312 and stent 302. Referring to FIG. 10A-D, an increase in rotation rate of element 308 from $R_1$ to $R_2$ causes element 308 to rotate ahead of stent 302 resulting in a shift of contact points between stent 302 and element 308. The relative rotation can continue as long the rotation rate of element 308 differs from element 310. The degree of relative rotation would depend on the length of the stent and the torsional stiffness of the stent in order to cause separation of the support elements.

For example, for a pulse represented by FIG. 10A, the final rotation rate $R_3$ is greater than $R_1$ which causes element 308 to continue to rotate ahead of or faster than stent 302. The final rotation rate must be the same for both spindles if the stent is keyed into element 308 for 1:1 rotation, otherwise the stent can be damaged through torsion. Similarly, for the pulse of FIG. 10D, element 308 continues to rotate ahead of or faster than stent 302 as long as the rotation rate is at $R_2$. For a pulse shown by FIG. 10B, the final rotation rate is less than $R_1$ which causes element 308 to rotate behind or slower than stent 302. The final rotation rate, $R_3$, is the same as the pre-pulse rotation rate, $R_1$, in FIG. 10C. Thus, element 308 stops rotating relative to stent 302 when the rotation rate of element 308 returns to $R_3$. After the pulse, element 308 has different contact points with stent 302.

As described above, pulses can be performed at a specified frequency resulting in a change in contact points at the specified frequency. Alternatively, pulses can be performed at irregular intervals.

Similar to the embodiment in FIG. 11A, contact points between stent 302 and elements 308 and 310 can be shifted by pulsing element 308 or 310 in a linear direction. The linear motors can provide linear pulses to elements 308 or 310. As above, a linear pulse is an axial translation of element 308 or 310.

The linear pulses tend to reduce or prevent sticking of the stent to elongate elements 312 or 314. Translation of support element 308, for example, inward toward stent 302 causes struts 302A of stent 302 to slide or ride upward along elements 312. Similarly, translation of support element 308 outward from the stent, causes struts 302A to slide or ride downward along elements 312. A representative linear pulse is shown in FIG. 12. The rate corresponds to the linear translation rate of support element 308 or 310 relative to an assembly that includes system 300 which translates back a forth during coating. For example, support member 308 can be pulsed inward toward stent 302 with a pulse having the functional form in FIG. 12. Support element 308 can be pulsed outward in a similar manner.

Pulses or a suitable combination of pulses can cause axial translation of supports 308 and 310 with respect to stent 302 in a number of ways. As described above, FIGS. 13A-H show the axial position of an end of support element 308 or 310 as a function of time.

Furthermore, translational pulses of elements 308 or 310 can be performed at a specified frequency resulting in a change in contact points at the specified frequency. Alternatively, pulses can be performed at irregular intervals.

In other embodiments, assembly 300 can include an element disposed axially within stent 302 at least between support element 308 and support element 310. Alternatively, the member may extend between spindle 304 and spindle 306. The member may include, but is not limited to, a rod or wire. The member may be coupled to the support members at each end in a manner than allows independent rotation of the rotary spindles.

In additional embodiments, assembly 300 can include only one rotatable support element, e.g., support element 308, with an opposing support element being rotationally fixed. Distal end 311 of stent 302 can fit loosely over an opposing support element so that there is not a 1:1 rotation of stent 302 with the support element. Such a support element can have a variety of shapes including those pictured in FIGS. 11A-B and FIGS. 14A-B.

A further aspect of the present invention relates to eliminating coating defects that can result from stent contact with supports, such as mandrels, during coating. Additional embodiments of the present invention involve selectively coating portions of a stent that have no contact points.

Figure 15A:
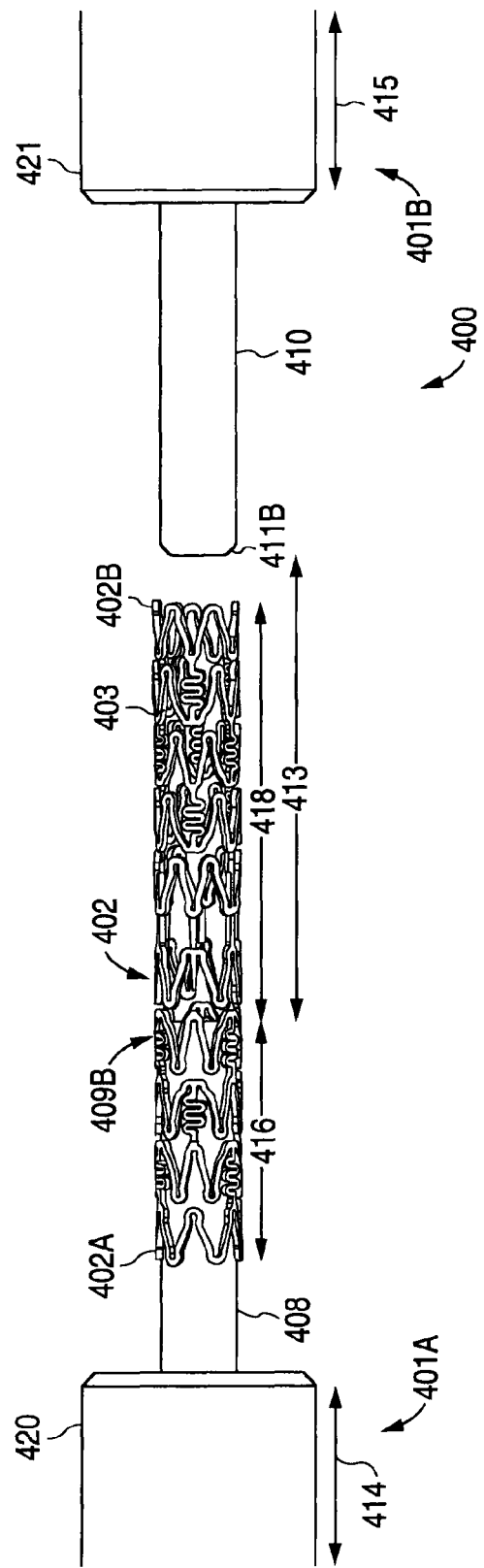
FIG. 15A depicts a side view of an embodiment of a stent support system for coating a portion of a stent that has no contact points.
Figure 15B:
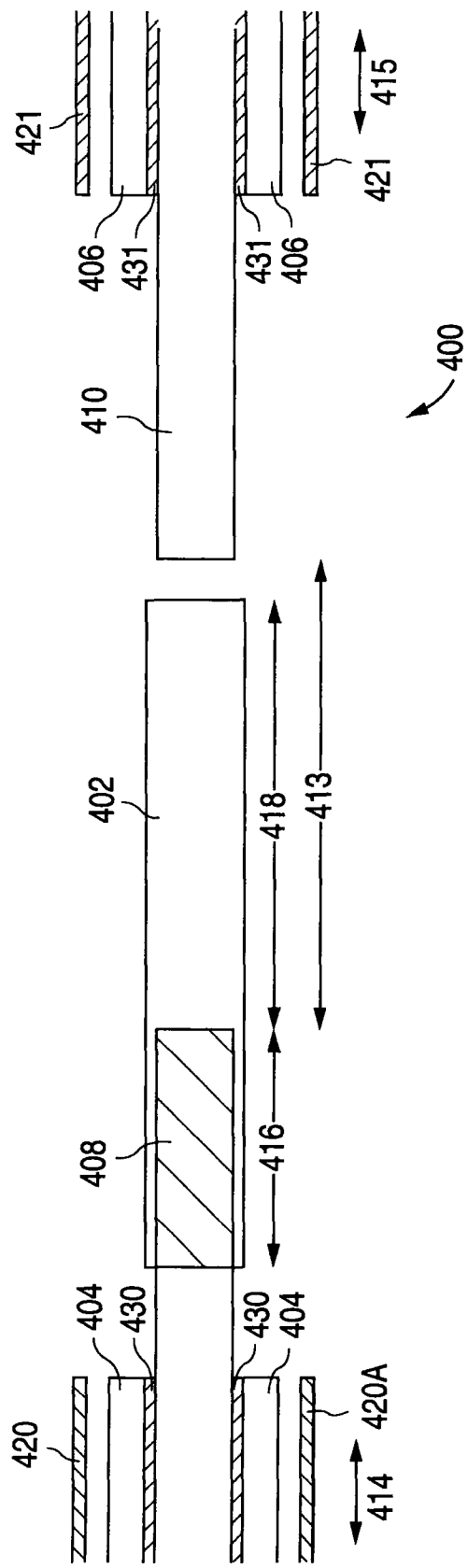
FIG. 15B depicts an axial cross-section of the stent support system of FIG. 15A.

FIGS. 15A-B depict views of an exemplary embodiment of a stent support assembly 400 for coating a stent 402 having a proximal end 402A and a distal end 402B. FIG. 15A depicts a side view of assembly 400 and FIG. 15B depicts an axial cross-section of assembly 400. As described below, assembly 400 is configured to selectively coat portions of stent 402 that have no contact points. An exemplary stent 402 has a geometry composed of a plurality of undulating and intersecting elements or struts 403.

As shown in FIG. 15B, assembly 400 includes a rotation spindle 404 and a rotation spindle 406 that can rotate independently of one another. A support mandrel 408 is coupled to rotation spindle 404 at a proximal end 409A of mandrel 408 as shown. A distal end 409B of mandrel 408 is free floating, i.e., not coupled or connected to another support element. A support mandrel 410 is coupled to rotation spindle 406 at a proximal end 411A of mandrel 410. A distal end 411B is free floating. Thus, distal end 409B of support mandrel 408 and distal end 411B of support mandrel 410 are separated by a gap 413. As described above, gap 413 is adjustable.

A masking sheath 420 is disposed over spindle 404 and can be translated axially over rotation spindle 404. A shuttle sheath 430 is positioned over support mandrel 408 which can axially translate over support mandrel 408. In a similar manner, shuttle sheath 431 is disposed over spindle 406 and shuttle sheath 431 is disposed over support mandrel 410.

Either or both rotation spindle 404 and rotation spindle 406 can be axially translated as shown by arrows 414 and 415, respectively. Prior to coating, stent 402 is loaded onto support mandrel 408 by sliding stent 402 onto support mandrel 408. Alternatively, stent 402 can also be loaded onto support mandrel 410. Prior to loading stent 402 on support mandrel 408, one or both of the rotation spindles can be axially translated to their maximum separation position or at least to a position that allows loading of stent 402.

As shown in FIGS. 15A-B, stent 402 is loaded so that a portion 416 of stent 402 is over support mandrel 408 and a portion 418 extends beyond distal end 409B of support mandrel 408. Portion 418 is free of contact points with support mandrel 408 and any other support element. Portion 416 can be long enough so that there is adequate support for portion 418, for example, so that there is no or substantially no sagging of portion 418. It is expected that the longer the stent, a larger percentage of the length of stent 402 should be over mandrel support 408. For example, portion 416 can be less than 30%, 40%, 50%, 60%, or 70% of the length of stent 402. It may be desirable for portion 418 to be as large as possible since, as described below, a coating material is applied to a majority of portion 418.

Figure 16A:
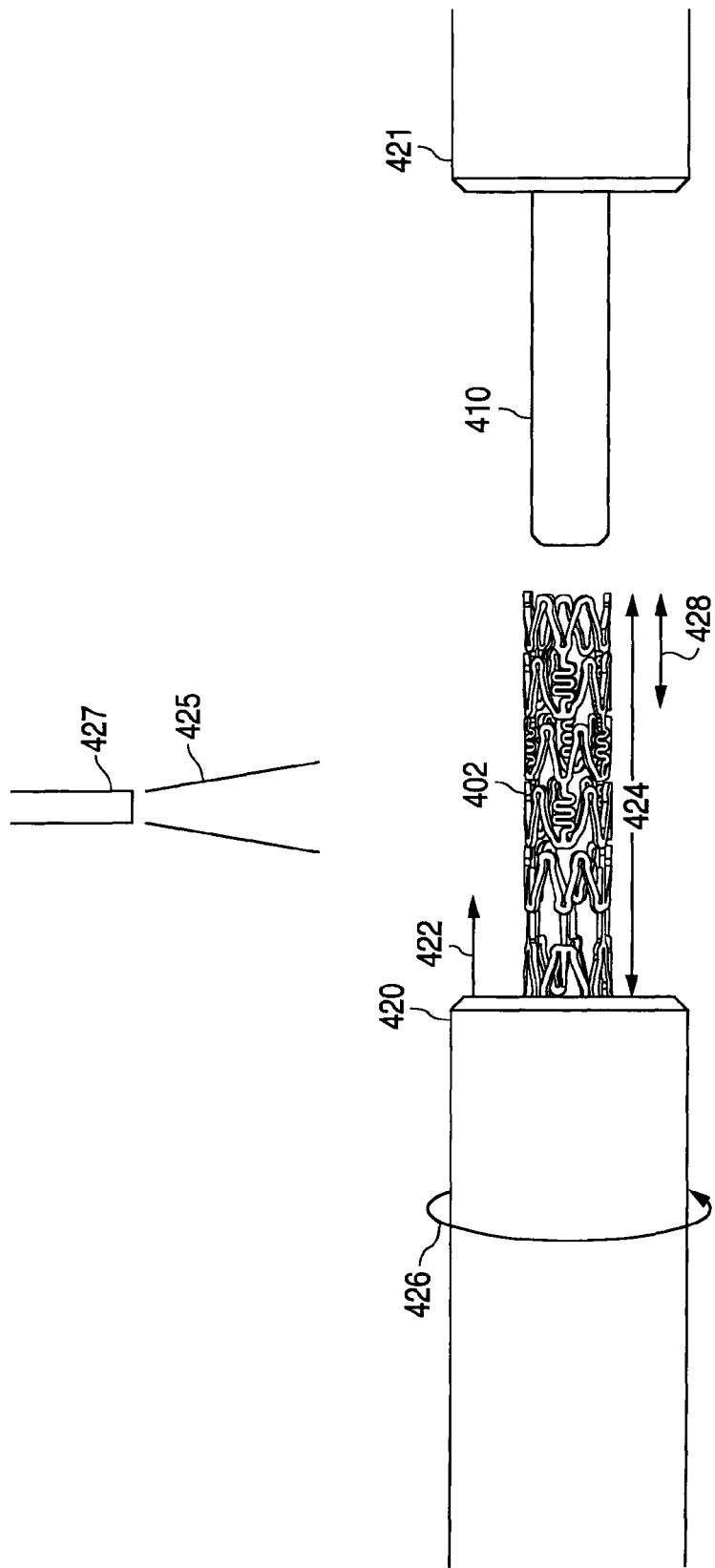
FIG. 16A depicts an alternative view of the stent support system of FIG. 15A.
Figure 16B:
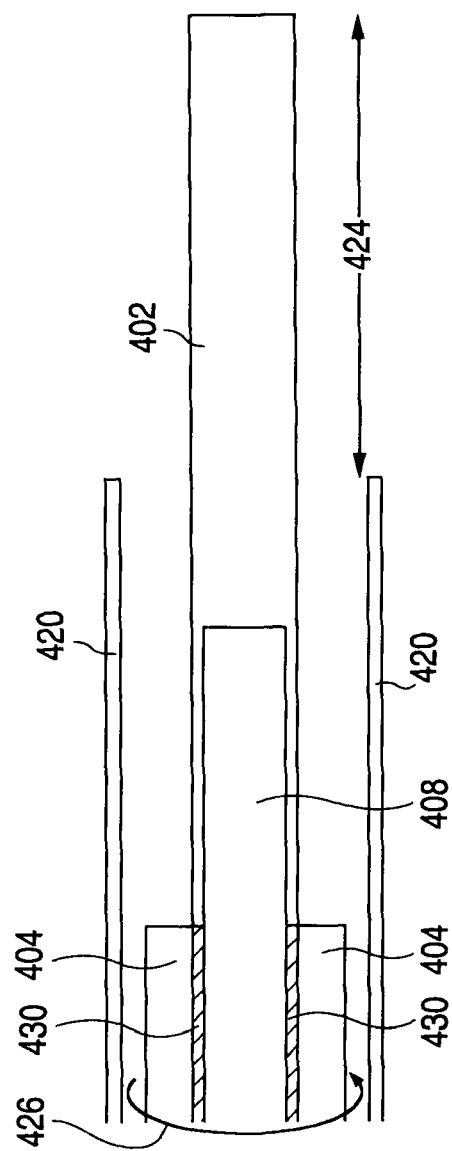
FIG. 16B depicts an axial cross-section of one side of the stent support system of FIG. 16A.

FIGS. 16A-B depict views of assembly 400 showing masking sheath 420 translated axially from rotation spindle 420, as shown by an arrow 422, to mask or cover at least portion 416 of stent 402 in FIG. 15A. FIG. 16A depicts a side view of assembly 400 and FIG. 16B depicts an axial cross-section of one side of assembly 400. As shown, a portion 424 is unmasked. Preferably sheath 420 masks portion 416 and a small axial section of portion 418 to inhibit or prevent exposure of portion 416 to coating material. For example, the small axial section may be less than 1%, 3%, 5%, 8%, 10%, or less than 15% of a length of stent 402.

After positioning masking sheath 420, a coating material 425 is applied to unmasked portion 424 from a spray nozzle 427 positioned above stent 402. Stent 402 is rotated by rotation spindle 404, as shown by an arrow 426 during coating. Additionally, stent 402 is axially translated by axially translating rotation spindle 404 along with masking sheath 420, as shown by an arrow 428, during coating. Alternatively or additionally, spray nozzle 427 can be translated along unmasked portion 424.

At least one pass of spray nozzle 427 from one end of portion 424 to the other can be made over stent 402. After a desired amount of coating material is applied to unmasked portion 424, the coating applied on stent 402 is dried according to methods known to a person of skill in the art or by methods disclosed herein. Stent 402 can be dried at the same location as it is sprayed or moved to a drying station (not shown). Alternatively, the coating can be dried at the same time it is being sprayed. The spraying-drying cycle can be repeated a number of times until a desired amount of coating material has been applied to the stent.

To coat the masked portion of stent 402, stent 402 is loaded onto support mandrel 410 by axially translating support mandrel 408 toward support mandrel 410, decreasing adjustable gap 413 shown in FIGS. 15A-B. Mandrel 408 is axially translated so that distal end 402B of stent 402 engages distal end 411B of mandrel 410. Distal end 411B is tapered to facilitate engagement of stent 402 on distal end 411B.

Figure 17B:
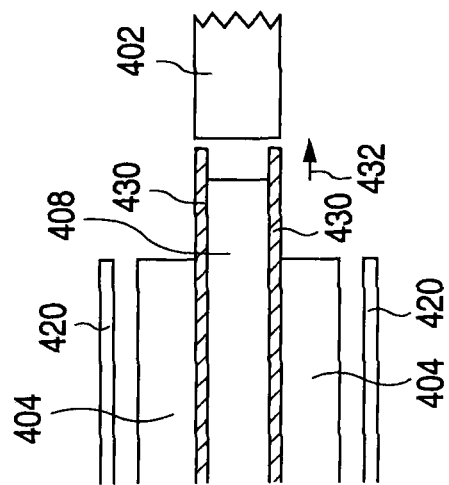
FIG. 17B depicts an axial cross-section of one side of the stent support system of FIG. 17A.

FIG. 17A depicts a side view of assembly 400 showing shuttle sheath 430 positioned over support mandrel 408 axially translated towards support mandrel 410 as shown by an arrow 432. FIG. 17B depicts an axial cross-section of one side of assembly 400 showing shuttle sheath 430 over support mandrel 408. As shuttle sheath 430 translates, it pushes against stent 402 at proximal end 402A so that stent 402 is pushed off support mandrel 408 and onto support mandrel 410.

As shown in FIG. 17A, stent 402 is positioned on support mandrel 410 in a manner that is similar to support mandrel 408. In particular, stent 402 is loaded on support mandrel 410 so that a portion 436 of the stent is over support mandrel 410 and a portion 438 extends beyond distal end 411B of support mandrel 410. Portion 438 is free of contact points with support mandrel 410 and any other support element. Portion 436 can be long enough so that there is adequate support for portion 438, for example, so that there is no or substantially no sagging of portion 438. Portion 438 includes at least the portion of stent 402 that was not coated while stent 402 was loaded on mandrel support 408.

In a manner similar to that described above, a masking sheath translates axially from rotation spindle 406 to mask or cover portion 436. After positioning the masking sheath, coating material 425 is applied to the unmasked portion from spray nozzle 427 positioned above stent 402. Stent 402 is rotated by rotation spindle 406 during coating. Additionally, stent 402 is axially translated by axially translating rotation spindle 406 during coating. Alternatively or additionally, spray nozzle 427 can be translated along an axis of the unmasked portion. At least one pass of spray nozzle 427 can be made over stent 402. After a desired amount of coating material is applied to the unmasked portion, the coating applied on stent 402 is dried. The spraying-drying cycle can be repeated a number of times until a desired amount of coating material has been applied to the stent.

After coating stent 402 on support mandrel 410, stent 402 is loaded back onto support mandrel 408 if it is desired to apply additional coating to portion 418. Stent 402 may be loaded back onto support mandrel 410 in a similar manner as the transfer of stent 402 from support mandrel 408 to support mandrel 410. For example, either or both of the support mandrels can be axially translated toward one another so that proximal end 402A of stent 402 engages distal end 409B of mandrel 408. Distal end 409B is tapered to facilitate engagement of stent 402 on distal end 409B. A shuttle sheath positioned over support mandrel 408 can push against stent 402 at proximal end 402B so that stent 402 is pushed off support mandrel 410 and onto support mandrel 408. The sequence of steps described above involving coating on support mandrel 408, drying the coated portion, transferring stent 402 to support mandrel 410, coating stent 402 on support mandrel 410, can be repeated a selected number of times until a specified loading of coating is applied to stent 402.

In some embodiments, support mandrels 408 and 410 could be covered, coated, or jacketed with a lubricious material, such as Teflon, to reduce or eliminate defects that could be caused by interaction of the inside diameter (ID) of stent 402 with the outside surface of the mandrels. Additionally, in one embodiment, the outside diameter of the mandrels can be sized to allow a slip or friction-fit so that there is a 1:1 rotation of stent 402 with the mandrels.

In alternative embodiments, stent 402 can be coated by sequential spray coating of any number of contactless portions of stent 402. For example, stent 402 can be disposed so that a proximal portion is over support mandrel 408 and a distal portion is over support mandrel 410 with a center portion having no contact with either mandrel. FIG. 18 depicts an embodiment for coating a central portion 440 of stent 402. Proximal and distal portions (not shown) of stent 402 are masked by masking sheaths 442 and 444. Masking sheaths 442 and 444 are disposed over proximal and distal portions of stent 402 after disposing the proximal and distal portions over support mandrel 408 and support mandrel 410, respectively.

Additional aspects of the present invention relate to devices and methods for supporting a stent during coating, processing, or handling that reduce or eliminate defects in the stent coating. Various embodiments include a system for supporting a stent having support members that contact proximal and distal portions of a stent that are connected with a connecting member that extends between the support members outside of and free of any contact with the stent.

Figure 19A:
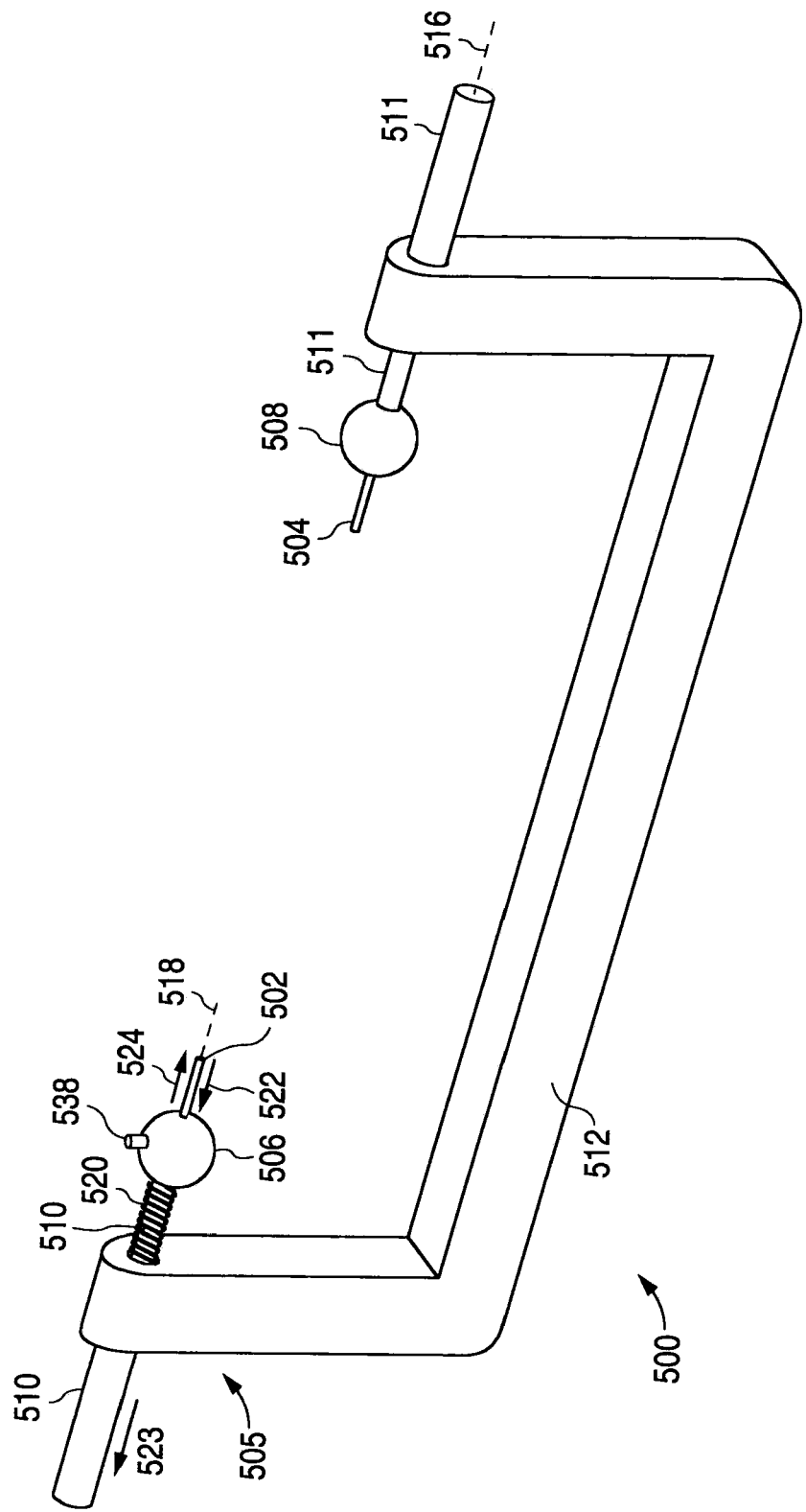
FIG. 19A depicts an exemplary embodiment of a stent support system.

FIG. 19A depicts a three-dimensional view of an exemplary embodiment of a stent support assembly 500. Support 500 includes pins or rods 502 and 504 which are coupled to collets 506 and 508, respectively. Collets 506 and 508 are coupled to a proximal and a distal end of a support bar 512, respectively. A stent can be supported on pins 502 and 504 between collets 506 and 508.

Figure 19B:
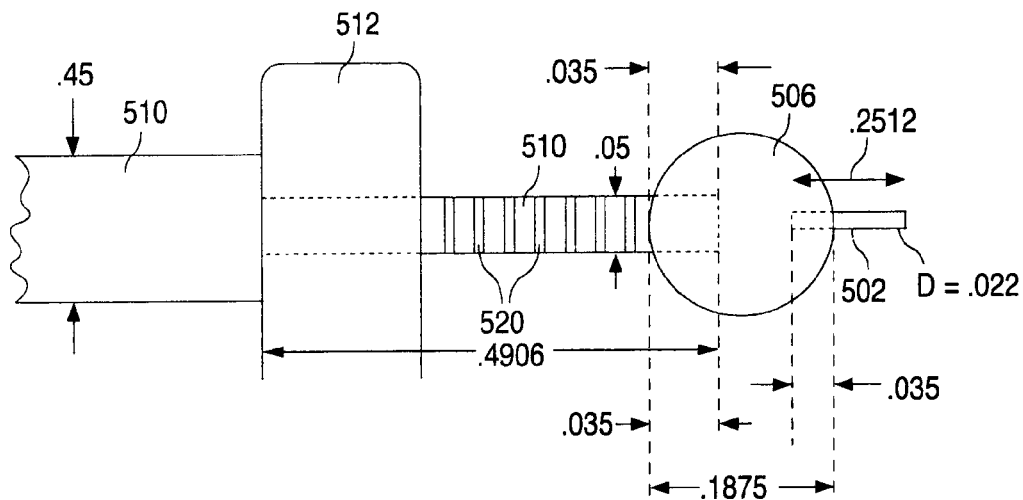
FIG. 19B depicts a close-up view of one side of the stent support system of FIG. 19A.

FIG. 19B depicts a close-up side view of a proximal end 505 of support 500. As depicted in FIG. 19B, pin 502 can be embedded in one side of collet 506 and rod 510 can be embedded in an opposite side of collet 506. Pin 504 and rod 511 can be coupled to collet 508 in a similar manner. Rod 511 extends through a distal end of support bar 512 and rod 510 extends through a proximal end of support bar 512. As shown in FIGS. 19A and 19B, rod 510 and rod 511 can have a larger diameter on the side opposite of collets 506 and 508, respectively. In other embodiments, rod 510 and rod 511 have the same diameter on both sides of collets 506 and 508, respectively.

Figure 20:
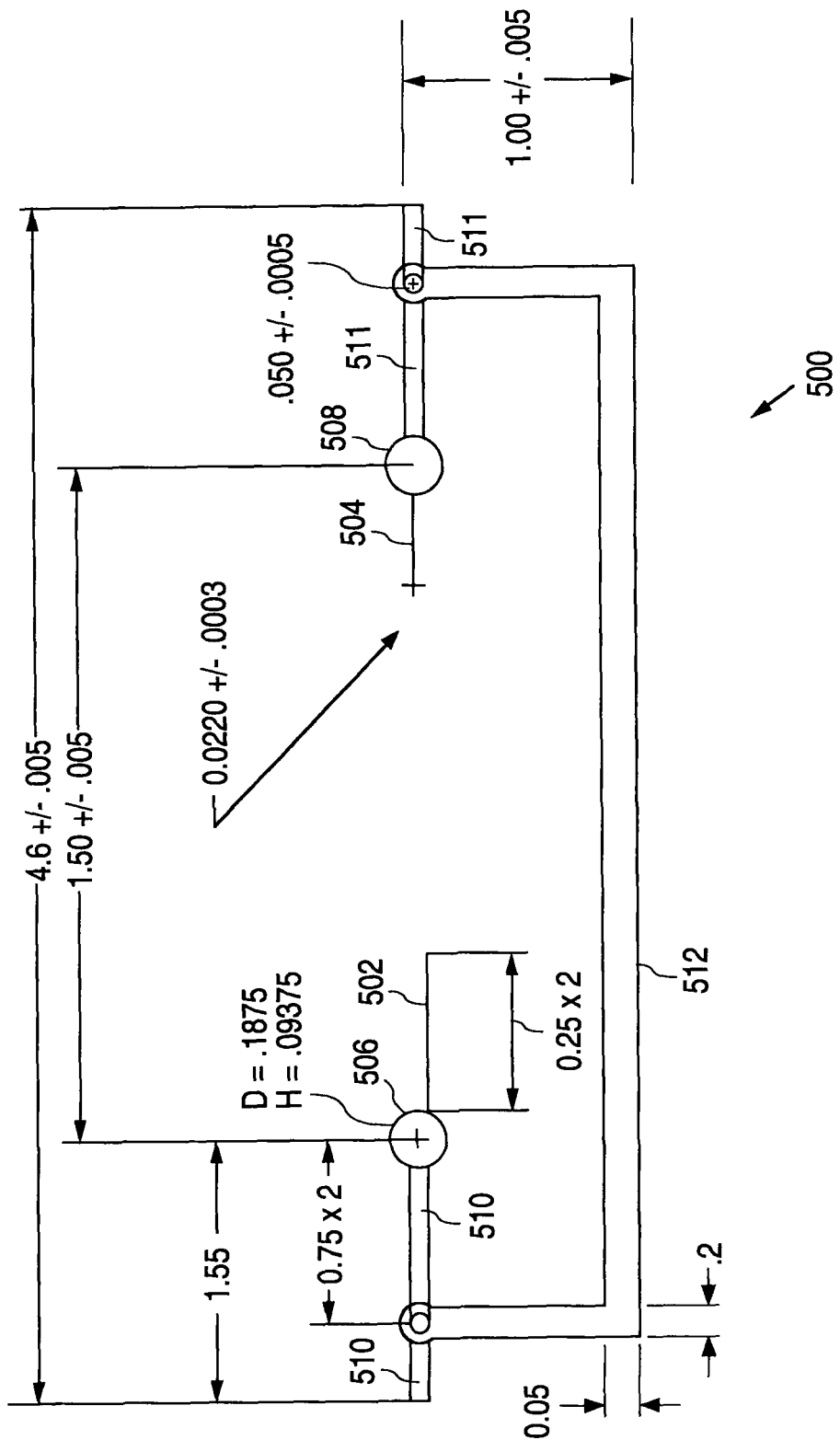
FIG. 20 depicts a side view of an exemplary embodiment of a stent support system.

FIGS. 19A and 20 show that support bar 512 is shaped in the form of a "C-clamp." Support bar 512 is designed so that it may be held, grasped, or manipulated during and/or before processing of a stent. Thus, other shapes of support bar 512 may be contemplated that allow support assembly 500 to be grasped, handled, or manipulated by a human hand or mechanically without contacting or interfering with a mounted stent. For example, support bar 512 can also be U-shaped.

In the exemplary embodiment depicted in FIG. 19A, pin 504, along with collet 508 and rod 511, are rotationally and axially fixed about and along axis 516. Pin 502, along with collet 506 and rod 510 are rotationally and axially movable about and along axis 518. As shown, rod 510 has a spring 520 that allows pin 502 to be retracted axially, as shown by an arrow 522, a specified distance. The retracted pin is then returned to and held at its original position by the force of spring 520. Retracting pin 502 allows a stent to be mounted or a mounted stent to be removed from support assembly 500. Pin 502 can be retracted by pulling rod 510 as shown by an arrow 523. Releasing rod 510 then allows pin 502 to return to its original position.

When pin 502 is retracted, a stent can be mounted by inserting a proximal end of a stent over pin 502 and a distal end of a stent over pin 504. Pin 502 is then pushed forward by the force of spring 520 to secure the stent on pins 502 and 504. Similarly, a mounted stent can be removed when pin 502 is retracted. The ability to load and unload a stent on a support with contact points limited pins 502 and 504, reduces or eliminates the potential for defects due to handling or manipulation of the stent.

FIG. 20 depicts a side view of an exemplary embodiment of support assembly 500. Representative dimensions are provided for support assembly 500. All dimensions are in centimeters. The representative dimensions are provided by way of example only and in no way are intended to limit support assembly 500.

Figure 21:
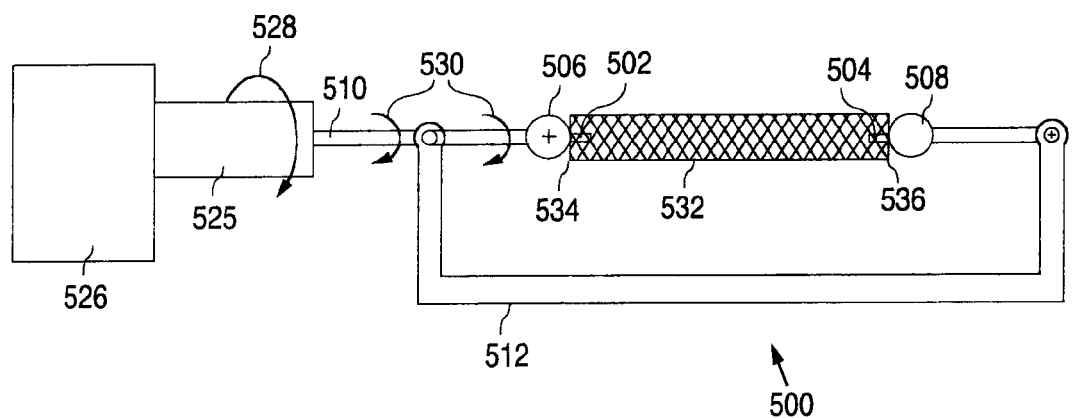
FIG. 21 depicts the stent support system of FIG. 19A coupled to a rotatable spindle.

FIG. 21 depicts a stent 532 mounted on support assembly 500. Stent 532 can be rotated by support 500, for example, during application of a coating to the stent. Rod 510 is coupled or engaged in a chuck in a rotatable spindle 525 that is coupled to a stationary support 526. Rotatable spindle 525 rotates rod 510 as shown by an arrow 528 which rotates rod 510 and collet 506 as shown by arrows 530.

A stent 532 can be mounted such that a length of stent 532 is less than a distance between collets 506 and 508 such that the stent can move from side to side during rotation. In another embodiment, a proximal end 534 and distal end 536 of stent 532 are at least partially in contact with a surface of collets 506 and 508, respectively. Collet 506 and pin 502 are positioned axially to contact stent 532 to allow a 1:1 rotation of collet 506 and stent 532. Collet 506 can have a protrusion or pin 538, as shown in FIG. 19A, positioned on its surface to reduce or prevent sticking of proximal end 534 to collet 506 during rotation. Protrusion 538 can make contact with a proximal end 534 that is sticking to collet 506, causing it break free.

In addition to use as a support during coating, support assembly 500 can be used as a support during various portions of stent processing. Support assembly 500 can be used generally for handling or manipulating a stent between and during processing steps. Support 500 can be used in operations such as weighing, inspection, and transport. When weighing a stent, the support bar can be held by hand and the spring-loaded end-pin can be grasped by the other hand.

For example, a coated stent 532 that is to be weighed can be loaded on a weigh pan by holding stent 532 over the weigh pan, retracting spring-loaded pin 502 and allowing coated stent 532 to be placed onto the weigh pan. Retracted pin 502 is allowed to return to a relaxed position. Thus, stent 532 may be loaded on the weigh pan without any additional contact of stent 532 with support 500. When the stent weighing process (or any other process) is complete, spring-loaded pin 502 can be retracted again to allow enough space for fixed pin 504 to be placed into distal end 536 of stent 532. Spring-loaded pin 502 can then be inserted into proximal end 534 of stent 532 to secure stent 532 onto support 500 for further transport, handling, or processing.

Further aspects of the present invention relate to devices and methods for supporting a stent during coating, processing, or handling that reduce or eliminate defects in the stent coating. Various embodiments include a system for supporting a stent with reduced contact points of a support with a stent. The stent support includes a spiral coil or spiral mandrel that can be disposed within a stent to support the stent during coating.

Figure 22A:
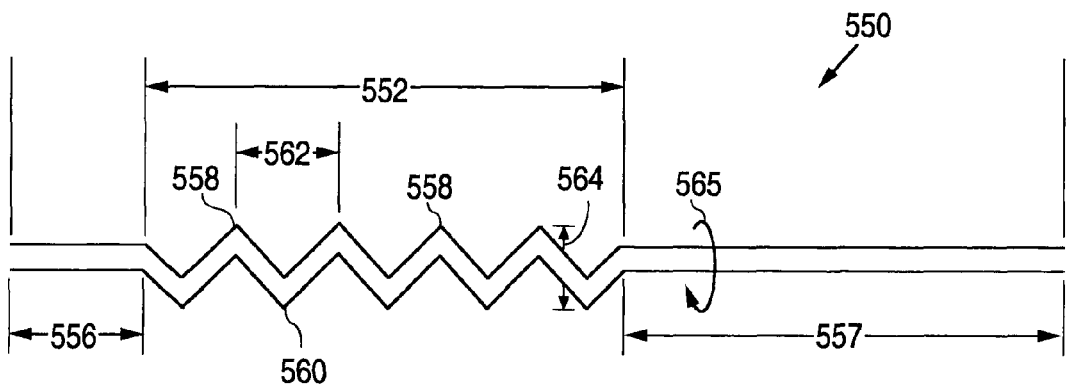
FIG. 22A depicts a two-dimensional view of a spiral coil support.
Figure 22B:
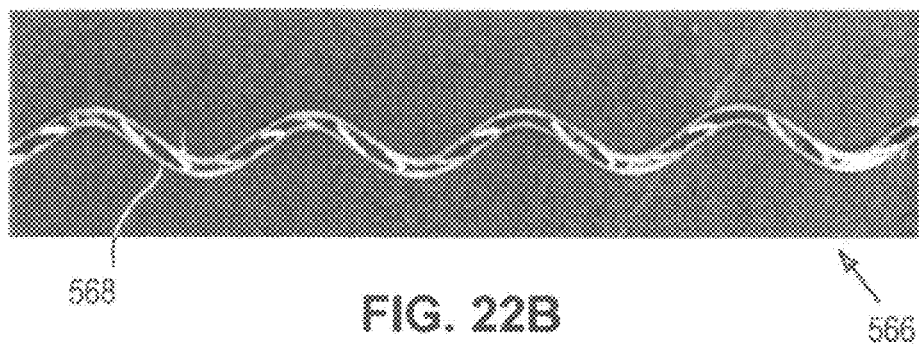
FIG. 22B depicts an illustration of a prototype of a spiral coil support.

FIGS. 22A and 22B depict exemplary embodiments of spiral coil supports for supporting a stent. FIG. 22A depicts a two-dimensional view of a spiral coil support 550 having a coiled portion 552, two straight portions 556 and 557 on either side of coiled portion 552. Peaks 558 of coiled portion 552 provide contact points with an inner surface of a stent to support the stent. An outside diameter 564 of coiled portion 552 from a peak 558 to a valley 560 is sized to be smaller than an inside diameter of a stent. Thus, as support 550 rotates the contact points alternate along the coil. Alternatively, diameter 564 is sized to obtain a friction fit or press fit between an inner surface of the stent and coiled portion 552. A "pitch" of a spiral coil refers to a distance from any point on the coil to a corresponding point on the coil measured parallel to the axis of the coil. For example, spiral coil support 550 has a pitch 562.

FIG. 22B depicts an illustration of a prototype of a spiral coil support having a pitch 568. The spiral coil is made from wire with a 0.017 inch outside diameter.

An advantage of a support as depicted in FIGS. 22A and 22B is that the number of contact points with a stent may be controlled by controlling pitch 562 of coiled portion 552. Increasing pitch 562 reduces the number of contact points of coiled portion 552 with a supported stent. However, the support provided to the stent is reduced by increasing the pitch. In one embodiment, a coil with a pitch of less than three, less than four, less than five, less than six, or more narrowly, less than seven pitch per inch may be used for coating a 28 mm stent. In an embodiment, the pitch may be controlled so that the total contact points may be less than three, less than four, less than five, or more narrowly less than seven.

An example of a spiral coil support 550 depicted in FIG. 22A has dimensions as follows: Length of straight portion 556=0.15 inch, Length of straight portion 557=1.05 inch, Length of coiled portion 552=2 inch, Diameter 564=0.05±0.005 inch, and Pitch 562=0.2 inch.

Figure 23A:
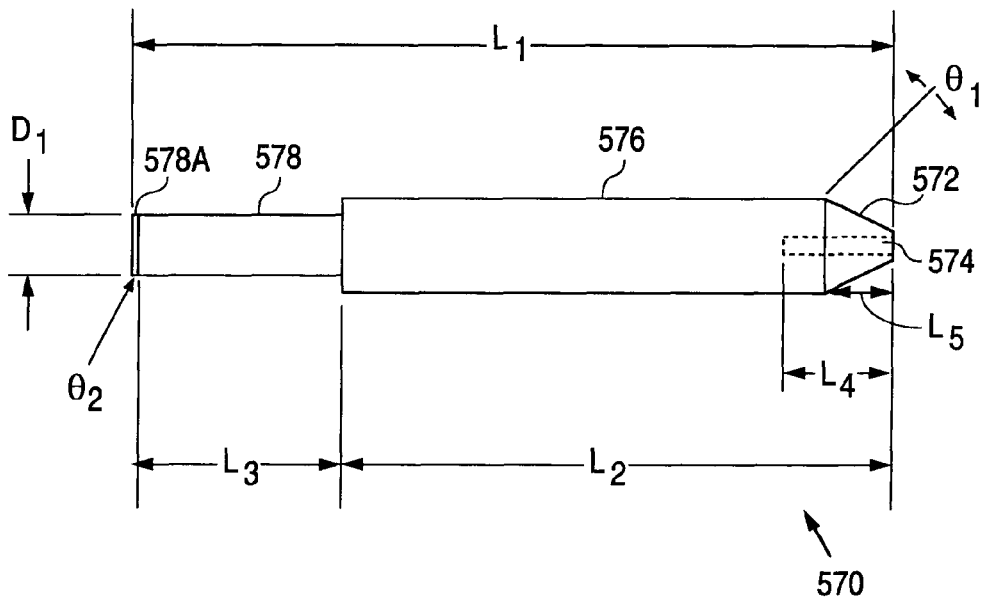
FIG. 23A depicts a holder for manipulating and positioning a spiral coil support.

FIG. 23A depicts a holder 570 for a spiral coil support for manipulating and positioning a spiral coil support. Holder 570 has a cylindrical cross-section. In an embodiment, holder 570 may be used to manipulate and position a spiral coil support before and after coating. Holder 570 can also support a spiral coil support during coating. Holder 570 includes a proximal tapered section 572 having a cavity or hole 574. Cavity 574 is capable of receiving a straight portion 556 or 557 of a spiral coil support. Straight portion 556 or 557 of a spiral coil support can be coupled within hole 574 by a press fit and/or by gluing. Straight portion 556 or 557 and hole 574 can also be threaded for a screw fit.

Figure 23B:
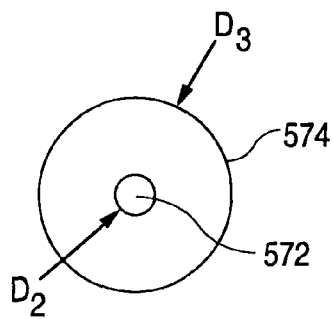
FIG. 23B depicts a radial cross-section of the front of the holder of FIG. 23A.
Figure 24A:
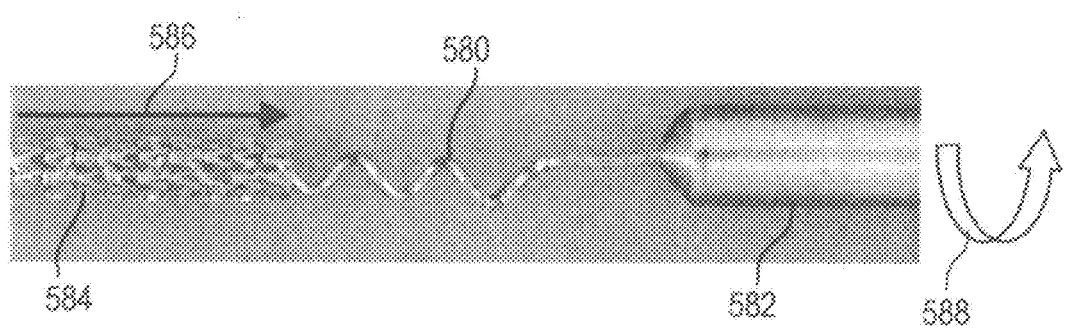
FIG. 24A depicts a picture of a spiral coil support supported by a holder.

FIG. 23B depicts a radial cross-section of the front of tapered section 572. A middle section 576 has a larger diameter than a distal section 578. Distal section 578 can be sized and adapted to engage into a rotatable spindle for rotating holder 570 during coating. For example, distal section 578 includes a tapered portion 578A for adapting to a support structure or rotatable spindle. An example of holder 570 depicted in FIGS. 22A-B has dimensions as follows: $L_1$=1.65 inch, $L_2$=1.2, $L_3$=0.45, $L_4$=0.125 inch, $L_5$=0.051, $D_1$=0.0995 to 0.1 inch, $D_2$=0.017 to 0.0175 inch, $D_3$=0.125 inch, $\theta_1$=45°, and $\theta_2$=45°. FIG. 24A depicts a picture of a spiral coil support 580 supported by a holder 582.

Figure 24B:
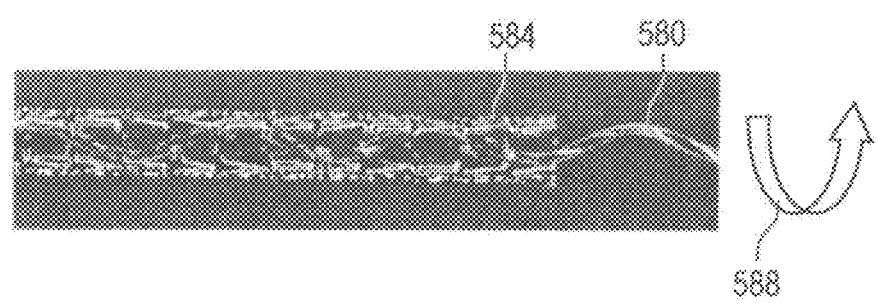
FIG. 24B depicts a picture illustrating a close-up view of a spiral coil support positioned within a stent.

Holder 582 is used to position support 580, as shown by an arrow 586, within a stent 584 to be coated. FIG. 24B depicts a close-up view of support 580 disposed within stent 584. When holder 582 is coupled with a rotating spindle, it can rotate support 580 and stent 584 as shown by an arrow 588.

Figure 25:
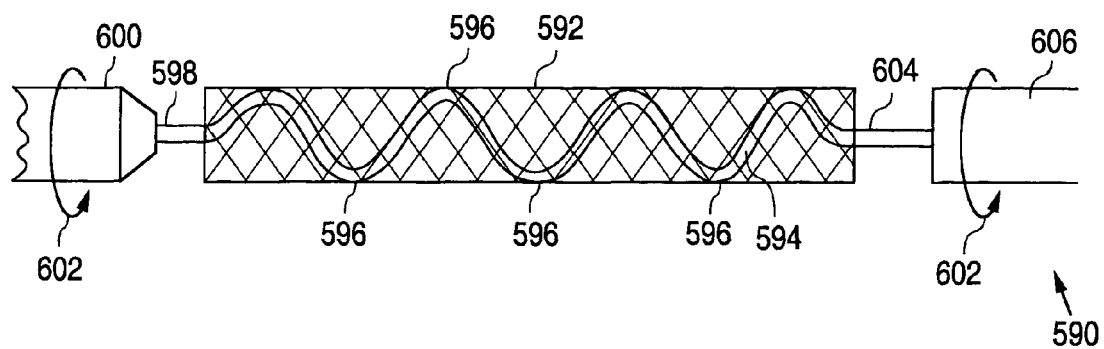
FIG. 25 depicts an axial view of a system for coating a stent supported by a spiral coil support.

FIG. 25 depicts an axial view of an assembly 590 for coating a stent 592 supported by spiral coil support 594. The coiled portion of spiral coil support 594 supports stent 592 at contact points 596. Straight portion 598 of spiral coil support 594 is coupled to a holder 600 like that shown in FIG. 23A. Holder 600 can rotate as shown by an arrow 602 which rotates support 594 and stent 592. A straight portion 604 can be coupled to a fixed or rotatable spindle or member 606. Assembly 590 can also axially translate stent 592 relative to a nozzle spraying coating material onto stent 592.

Figure 26A:
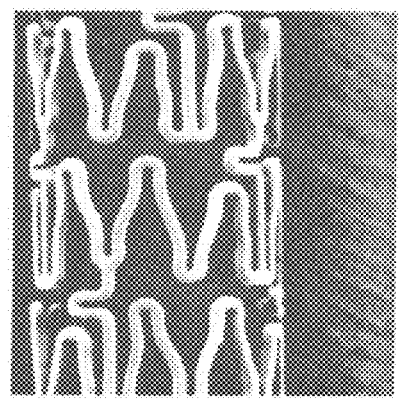
FIGS. 26A-D depict scanning electron micrograph (SEM) images of 28 mm stents coated using a spiral coil support to support the stent during coating.
Figure 26B:
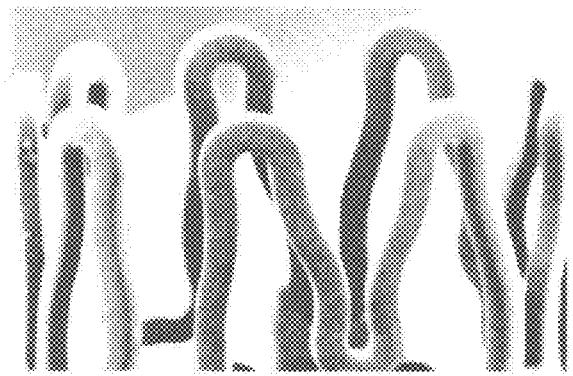
Figure 26C:
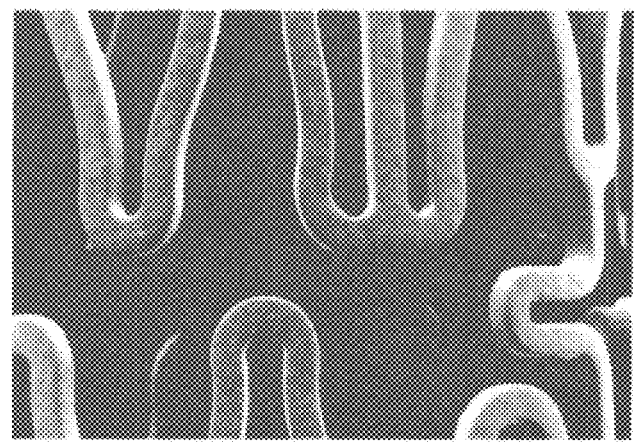
Figure 26D:
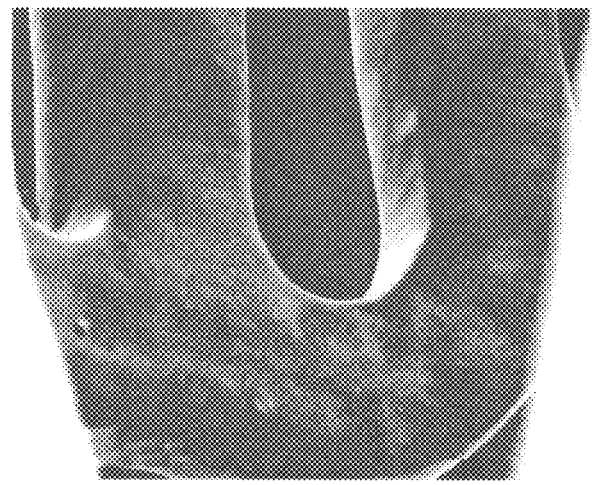

FIGS. 26A-D depict scanning electron micrograph (SEM) images of 28 mm stents coated using an embodiment of a spiral coil support or spiral mandrel. The stent used in the examples are Xience V medium stent obtained from Guidant Corporation in Santa Clara, Calif. The pump rate of coating material during spraying of the stent was 3 ml/hr and the rotation rate of the stent was 100 rpm. The drying nozzle was set to 55° C. at an air pressure of 20 psi. FIG. 26A depicts an outside surface of a coated stent. FIG. 26B depicts an end ring of a coated stent. FIG. 26C depicts a close-up view of an outside surface of a coated stent. FIG. 26D depicts a close-up view of an inside surface of a coated stent.

Figure 27:
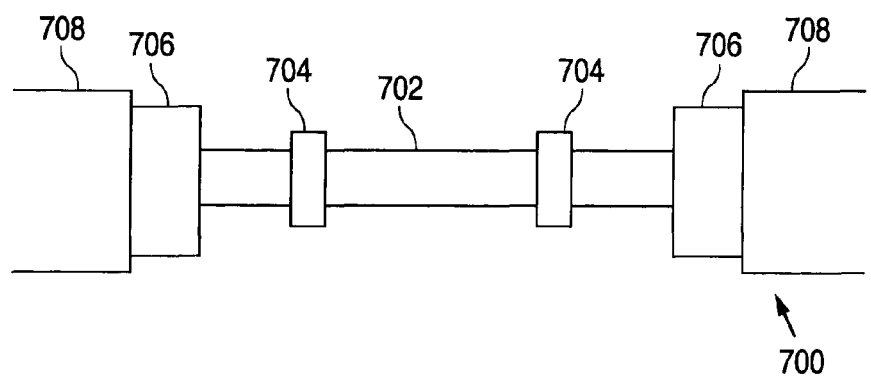
FIG. 27 depicts a stent mounted on a stent support system.

Another aspect of the present invention relates to a device that allows reduced contact area between a support for a stent and the ends of a stent during coating of the stent. FIG. 27 depicts a side view of a stent support assembly 700 including a mandrel 702 and support collets 704 for supporting a stent. Assembly 700 also includes collets 706 for securing a stent mounted over a mandrel in an axial direction. One or both of members 708 can be rotatable spindles for rotating mandrel 702 which rotates a stent mounted on mandrel 702. At least one of members 708 can be rotationally and axially fixed.

As indicated above, it is generally desirable to minimize the contact area between an end of a stent and collets 706 to reduce or prevent coating defects. Additionally, minimizing such contact area tends to reduce undesirable wicking or flow of coating material from the stent to the collets. Contact points can create defects such as uncoated or insufficiently coated areas on a stent surface. Wicking can also result in uncoated or insufficiently coated areas.

It is desirable to minimize the interface between the end of a stent and the apparatus supporting the stent end during the coating process to minimize coating defects. Accordingly, the present invention provides for a device for supporting a stent during the coating application process. The invention also provides for a method of coating the stent supported by the device.

Various embodiments of the present invention include a collet that is shaped so as to minimize contact area of a stent end with a surface of the collet. Certain embodiments of the collet have an end surface for contacting a stent end that includes a raised or projecting portion and a flat or relatively flat portion. In one embodiment, the projecting portion may have at least three segments radiating from a center to the edge of the surface. The thickness of the segments in a plane of the surface may decrease from the center to the edge of the surface. Additionally, a height of the projecting portion perpendicular to the surface may decrease from the center of the surface to the edge.

Figure 28A:
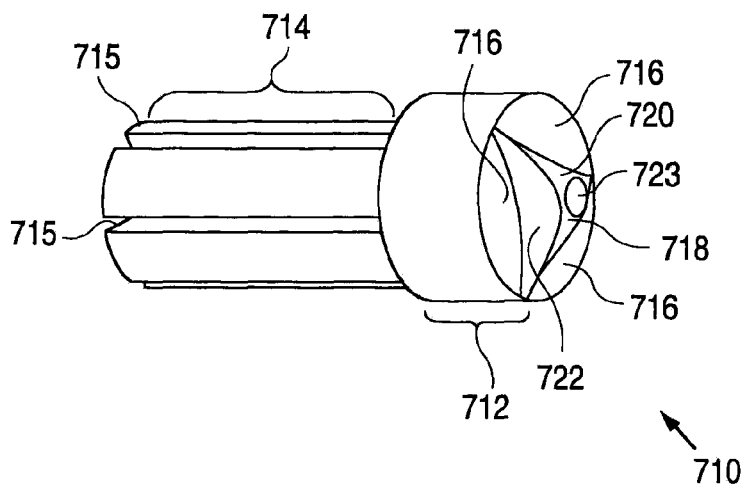
FIGS. 28A-D depict an exemplary embodiment of a collet.

FIGS. 28A-D depict an exemplary embodiment of a collet 710 having a head section 712 and a body section 714. FIG. 28A depicts a three-dimensional view of collet 710. An end surface of head section 712 has flat portions 716 divided into sections by a projecting portion 718. Projection 718 has a top surface 720 and a sidewall surface 722 with a hole 723. A mandrel for supporting a stent may be inserted and disposed in hole 723.

Body section 714 has slots 715 running parallel to an axis of body section 714. Slots 715 are designed to allow collet 710 to engage and couple to a rotatable spindle or other support structure. In one embodiment, body section 714 has six slots 715 spaced 60° apart. In other embodiments, body section 714 has seven, eight, nine, or ten slots.

Figure 28B:
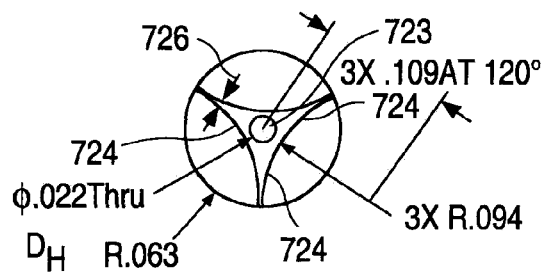

FIG. 28B depicts a two-dimensional radial projection of the end surface of collet 710 which shows three segments 724 of projection 718 radiating from the center of the end surface of collet 710 to the edge of the end surface. A thickness 726 of segments 724 of projection 718 decrease from the center to the edge of the surface. Adjacent segments 724 may radiate in directions that are 120° apart. Other embodiments may include four, five, or six segments radiating from the center to the edge of the end surface spaced apart, for example, by 90°, 72°, or 60°, respectively.

Figure 28C:
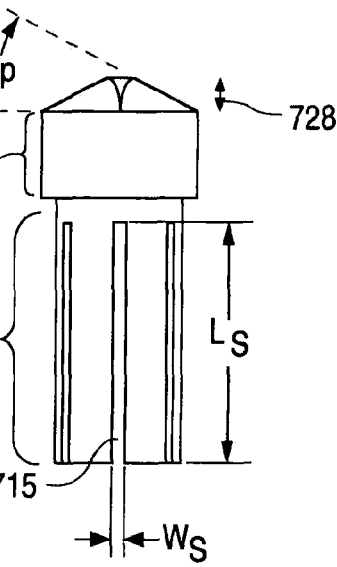
Figure 28D:
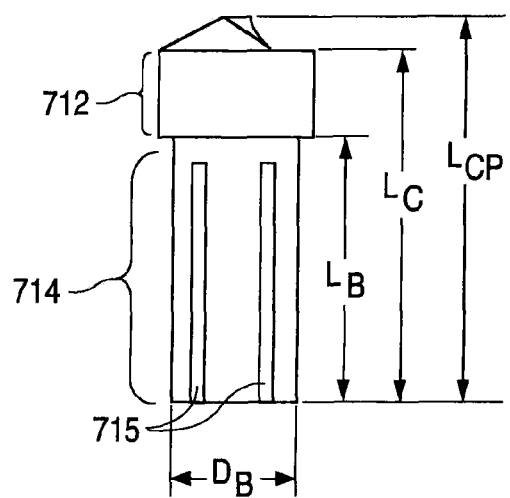

FIGS. 28C-D depict side views of collet 710. FIG. 28C depicts a view that is parallel to a length of one of segments 724. As shown in FIG. 28C, segments 724 have a pitch, $\theta_P$, which facilitates self-centering of the stent on the surface of the collet. In one embodiment, $\theta_P$ can be 30°. In other embodiments, $\theta_P$ can be greater than 30°, greater than 45°, or greater than 60°. FIG. 28D depicts a view facing along a direction that is between two adjacent segments 724. As shown in FIGS. 28A, 28C, and 28D, a height 728 of segments 724 decrease from the center to the edge of the surface.

In some embodiments, a radius of collet 710 may be sized so that stent ends are in contact with segments 724 near the edge of the surface of the end of collet 710. Segments 724 are relatively thin near the edge of the surface resulting in a relatively small contact area of the stent end with the collet. Thus, wicking of coating material from the stent to collet 710 is relatively low or nonexistent. Also, defects due to contact of the stent with collet 710 tend to be reduced or eliminated. Additionally, the decrease in height outward from the center tends to allow the stent to center itself on the surface which results in a consistent contact area between the stent and collet 710.

An example of collet 710 depicted in FIGS. 28A-D has the following dimensions: $W_S$=0.10 inch, $D_H$=0.022 inch, $D_B$=0.099 inch, $L_B$=0.22 inch, $L_C$=0.29 inch, and $L_{CP}$=0.32 inch.

Figure 29A:
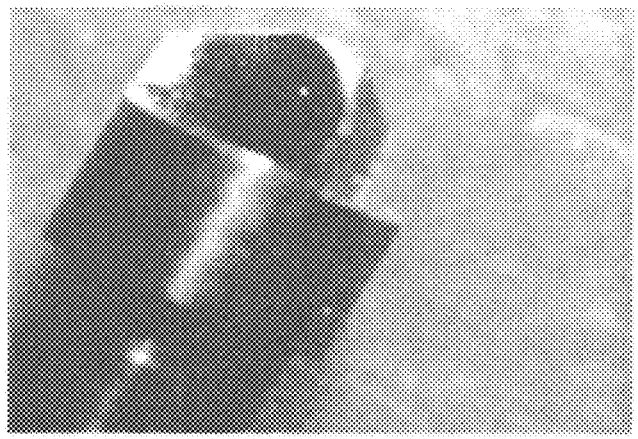
FIGS. 29A-B depict photographs with side views of an embodiment of a collet according to the present invention.
Figure 29B:
Figure 29C:
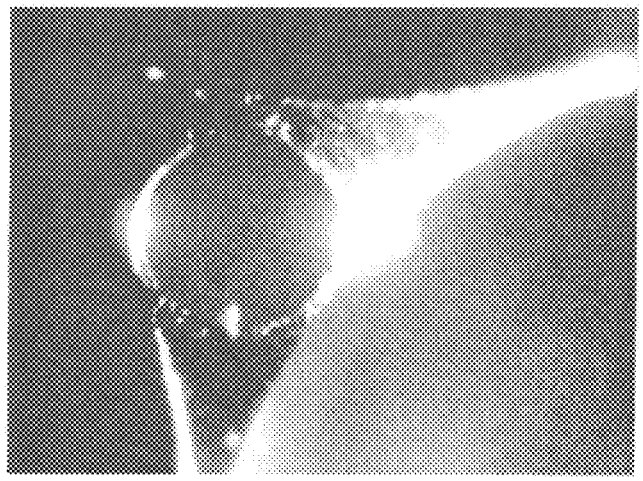
FIGS. 29C-D depict photographs with overhead views of an embodiment of a collet according to the present invention.
Figure 29D:
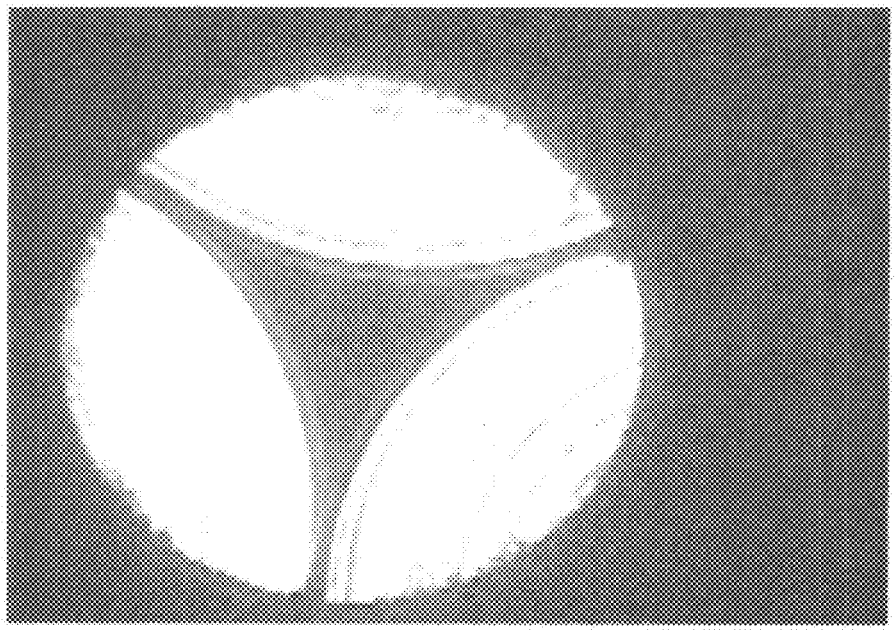
Figure 29E:
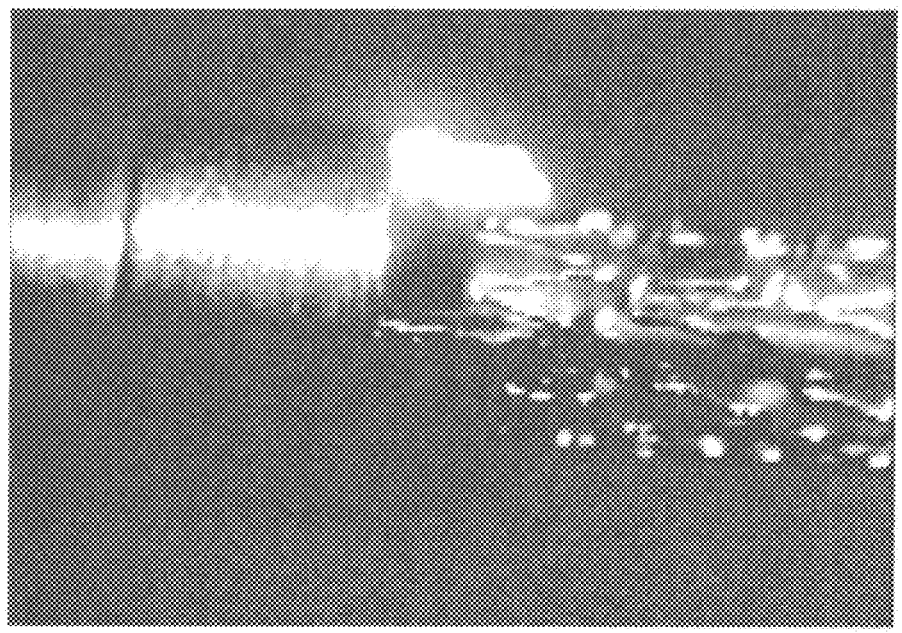
FIG. 29E depicts a photograph with a view of an embodiment of a collet according to the present invention with a stent mounted on the collet.

FIGS. 29A-E depict photographs of an embodiment of the collet according to the present invention. FIGS. 29A-B depict photographs with side views of the collet and FIGS. 29C-D depict photographs with overhead views of the collet. FIG. 29E depicts a photograph of a stent mounted on the collet.

Another aspect of the present invention relates to a method and device that reduces operator or machinery contact with a mandrel that supports a stent during processing. Stent handling or manipulation, whether manual or automated, risks exposing a stent to damage and/or contamination with undesired impurities. Embodiments of the present invention tend to reduce or eliminate damage to a stent and/or stent coating that may be caused by handling or manipulation of a stent during processing. Damage can result from contaminants or undesired contact with surfaces. Such embodiments also reduce or eliminate damage resulting from exposure to a stent to undesired contaminants.

As described above, coating a stent requires a number of processing steps which involve handling and manipulation of a stent. The process involving application of a coating, a drug-polymer coating, for example, may include loading or mounting a stent on a mandrel. A conventional mandrel for supporting a stent during processing is coupled mechanically through direct or indirect physical contact to fixtures and/or rotatable spindles. For example, mandrel 702 in FIG. 27 is coupled mechanically through direct physical contact to members 708. Such mechanical rotation devices typically require lubricants or other substances for their normal operation. During the course of processing a stent, such lubricants or substances can come into contact with a coated stent.

Furthermore, as discussed above, a coating is typically applied in stages with a drying step in between stages. The application step and drying step are repeated until a desired weight or loading of coating on the stent is achieved. After some or all of the drying steps, the stent may be weighed. When the application-drying stages are completed, the stent is typically dried in an oven to remove all or substantially all of the solvent remaining in the coating.

In conventional coating systems, the above-described procedure can require handling and manipulation of a mandrel holding the stent. For instance, after application of a coating layer, the mandrel may be moved to a drying station. The drying station, for example, may include a nozzle blowing a stream of heated gas on the coated stent. A stent may be transferred to an oven for a drying, which can be the final drying step. In addition, after one or more of the drying steps, a stent may be transferred to a weighing station, unloaded from a mandrel, and transferred to a scale for weighing. During each of these handling or manipulation procedures, the stent and/or stent coating can be damaged through contact with surfaces or exposure to undesired substances.

Embodiments of a system including a mandrel that can support a stent without physical or mechanical contact with other machines or devices during processing are described herein. In some embodiments, the mandrel can contact, hold, translate and/or rotate a stent. Limited operator or machinery contact with the mandrel reduces or eliminates damage or defects to a stent and/or stent coating that occur during processing. The mandrel of the system is supported, translated, and/or rotated through magnetic levitation.

Figure 30:
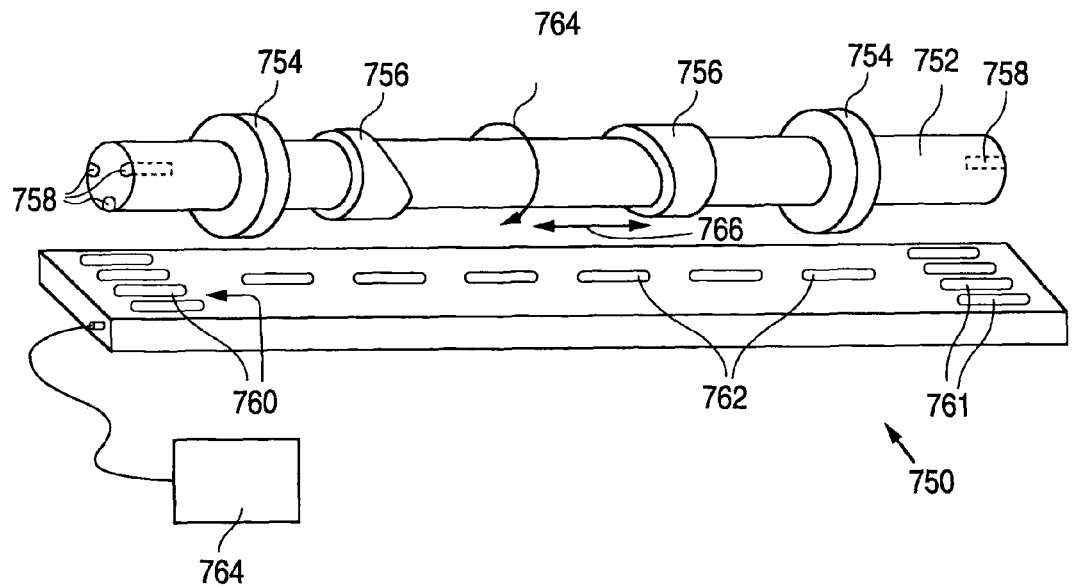
FIG. 30 is an exemplary embodiment of a stent support system with a mandrel capable of magnetic levitation.

FIG. 30 is an exemplary embodiment of a system 750 having a mandrel 752 that is supported by magnetic levitation. Mandrel 752 includes removable collets 754 and support collets 756. A stent can be placed over mandrel 752 between removable collets 754 and supported directly on support collets 756. A diameter of support collets 756 can be sized to be slightly smaller than an inside diameter of a stent to be coated.

Mandrel 752 includes permanent magnets 758 embedded within a proximal and a distal end of mandrel 752. "Permanent magnets" refer to materials that possess a magnetic field which is not generated by outside influences such as electricity. In some embodiments, mandrel 752 can include magnets 758 in only one end of mandrel 752. In other embodiments, magnets 758 can be embedded or disposed at other positions along mandrel 752.

As shown in FIG. 30, mandrel 752 includes three magnets at each end. Generally, a mandrel 752 can include at least one magnet. In some embodiments, mandrel 752 can include more than four or more than five magnets. The size, number, and location of the magnets may be modified to obtain the desired movement of mandrel 752 as described below.

System 750 further includes electromagnetic coils 760, 761, and 762 positioned adjacent to mandrel 752. Coils 760, 761, and 762 are electrically connected to an electromagnetic power supply 764 which provides power to coils 760, 761, and 762 to generate an electrical field. Electromagnetic coils 760 and 761, for example, generate an electrical field that allows the magnets 758 to support or levitate mandrel 752 without the physical contact with fixtures or members such as members 706 and 708 in FIG. 27. The absence of a mechanical coupling between mandrel 752 and a support member eliminates the need for lubricants or other substances that may be required and that can contaminate a stent or stent coating.

Power supply 764 further includes polarity switching equipment. The polarity switching equipment induces polarity changes in the electromagnetic field generated by coils 760, 761, and 762 in a way that induces movement of magnets 758 to move mandrel 752 in a selected manner. For example, coils 760 and 762 can induce rotation of mandrel 752 as shown by an arrow 764 to rotate a stent during application of coating material to the stent. Also, coils 762 can induce translation of mandrel 752 as shown by an arrow 766.

Figure 31:
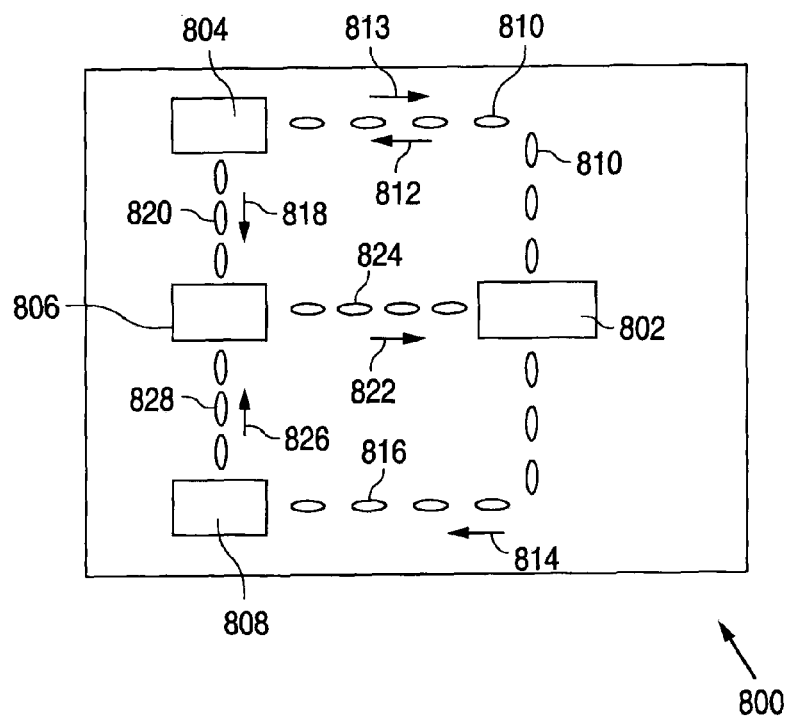
FIG. 31 depicts an overhead view of a coating system illustrating stations corresponding to various processing steps.

In additional embodiments, a coating system can use magnetic levitation to rotate or translate a stent during or between processing steps. FIG. 31 depicts an overhead view of a coating system 800 illustrating stations corresponding to various processing steps. A coating station 802 is for application of a coating material, such as a polymer-solvent mixture, to a stent. A stent mounted on a mandrel, including magnets, may be rotated and translated under a spray nozzle using magnetic levitation, as described above. Electromagnetic coils for use in the magnetic levitation can be powered by a power supply (not shown).

After application of a coating layer at station 802, the stent can be transferred to a drying station 804 that includes a nozzle that blows a stream of heated gas on the coated stent. The stent can be translated to and from station 802 and station 804 as shown by arrows 812 and 813 using magnetic levitation induced by coils 810 than run between the stations.

Additionally, the stent can be transferred to a drying station 808 for a final drying step. Drying station 808 may include an oven for drying the stent. The stent can be translated from station 802 to station 808 as shown by an arrow 814 using magnetic levitation induced by coils 816 than run between the stations.

A stent mounted on the mandrel can also be translated, as shown by an arrow 818, using magnetic levitation induced by coils 820 from station 804 to a weighing station 806 after the coating on the stent is dried at station 804. After weighing the stent at weigh station 806, the stent can then be translated back to coating station 802, as shown by an arrow 822, using magnetic levitation induced by coils 824. In addition, the stent can also be translated, as shown by an arrow 826, using magnetic levitation induced by coils 828 from station 808 to weighing station 806 after the coating on the stent is dried at station 808.

In other embodiments, a stent loaded on a magnetic mandrel can be translated to other processing stations or steps than those depicted in FIG. 31.

Purification of Coating Polymers

It is important to control the raw material purity of coating polymers for medical devices such as stents. A potential problem with polymers used in coating applications of stents is that such polymers can contain impurities that trigger adverse biological responses to the stent when implanted into a biological lumen. The polymers can contain impurities such as catalysts, initiators, processing aids, suspension aids, unreacted monomers, and oligomers, or other low molecular weight species, even though the polymer is sold as a "medical grade" polymer by the manufacturer. Thus, there tends to be a need to purify polymers used in coating applications. Various embodiments of the present invention relate to purifying such polymers.

It is desirable that after a polymer has been purified for the polymer to be substantially biologically inert. "Purified" refers to a polymer that has had impurities removed or significantly reduced. "Impurities" refer to traces of catalysts, initiators, processing aids, suspension aids, unreacted monomers, and oligomers, or other low molecular weight species, or any other chemical remaining in the polymer, that can cause or effectuate an adverse biological response greater than which would occur if the impurity is removed or significantly reduced. For example, "medical grade" poly(n-butyl methacrylate) (PBMA) can contain impurities such as suspension aids (e.g., starch) and unreacted monomers.

"Biologically inert" refers to a material that does not elicit a significantly greater adverse biological response than a biocompatible material, such as stainless steel, when implanted into a body vessel. Examples of biocompatible materials include metals such as stainless steel, titanium, and Nitinol, and organic materials such as collagen, fibronectin, polyethylene glycol, polysaccharides, TEFLON, silicone and polyurethane.

The coating for a stent including the purified polymer can have a drug-polymer layer, an optional topcoat layer, and an optional primer layer. The drug-polymer layer can be applied directly onto the stent surface to serve as a reservoir for a therapeutically active agent or drug which is incorporated into the drug-polymer layer. The topcoat layer, which can be essentially free from any therapeutic substances or drugs, serves as a rate limiting membrane for controlling the rate of release of the drug. The optional primer layer can be applied between the stent and the drug-polymer layer to improve the adhesion of the drug-polymer layer to the stent.

In one embodiment, poly(vinylidene fluoride-co-hexafluoropropene) copolymer (PVDF-HFP) (e.g., SOLEF 21508, available from Solvay Solexis PVDF, Thorofare, N.J.), can be used as a polymer for a drug-polymer layer or matrix. Polybutyl methacrylate (PBMA) can be used as the primer to improve adhesion between the metallic stent and the drug-polymer layer or matrix.

By using the methods described herein, the polymer for the drug-polymer layer can be purified to remove a significant amount of residual catalysts, initiators, processing aids, suspension aids, unreacted monomers, and oligomers or other low molecular weight species. Certain embodiments of a method of purifying a polymer mass may include washing the polymer mass with a solvent that dissolves an impurity, but not the polymer. The impurities, such as low molecular species including unreacted monomers and oligomers, should be miscible or substantially miscible in the solvent, while the polymer should be immiscible or substantially immiscible in the solvent.

In some embodiments, it may be advantageous for a solvent for use in purifying PVDF-HFP to have the following properties: (1) capable of swelling, but not dissolving PVDF-HFP; (2) capable of dissolving contaminants such as mineral oil; (3) the boiling temperature is low enough so that a solvent-washed polymer can be dried without using a convection oven; and (4) safety—Class III or Class II on the International Conference on Harmonization (ICH) Guidance list.

Representative examples of some solvents that may be used to purify PVDF-HFP include, but are not limited to, acetonitrile (ACN), isopropyl alcohol (IPA), methyl acetate (MA), ethyl acetate (EA), isopropyl acetate (ISPA), propyl acetate (PA), and mixtures of ethyl acetate and ethanol. The suitability of the above solvents for purifying PVDF-HFP can be evaluated by measuring the swelling of PVDF-HFP and the removal of contaminants from PVDF-HFP. The above-listed solvents were pre-screened by examining the physical parameters listed in Table 3.

TABLE 3

Physical parameters of the solvents evaluated for purification of PVDF-HFP.

| | ACN | IPA | MA | EA | EA/EtOH* (75/25) | EA/EtOH (50/50) | EA/EtOH (25/75) | ISPA | PA |
|---|---|---|---|---|---|---|---|---|---|
| ICH | II | III | III | III | III | III | III | III | III |
| b.p. (° C.) | 82 | 82 | 57 | 76 | NA | NA | NA | 87 | 102 |
| Effect PVDF | Swell | Swell | Dissolve | Dissolve 40% | Swell | Swell | swell | swell | swell |
| Mineral oil | <0.02% soluble | Not soluble | soluble | soluble | soluble | Not soluble | Not soluble | soluble | soluble |

*the boiling point for ethanol is 78° C.

Based on the pre-screening data listed in the above table, the following solvents were selected for further study of the swell parameters of PVDF-HFP. These include 1) ACN; 2) IPA; 3) EA; 4) ISPA 5) EA/EtOH (75/25).

The swelling of PVDF-HFP was determined as a function of time. Two methods were used to measure the PVDF-HFP swell ratio in the solvents: size measurement and weight measurement. Prior to contacting a sample of PVDF-HFP with a solvent, a sample pellet of PVDF-HFP was weighed and pictures were taken by a light microscope. The diameter of the pellet was measured from the digital image. This measured diameter is the data for time zero.

The sample pellet was then placed into a vial containing about 5 grams of a selected solvent and shaken on a shaker table at 480 rpm. At selected time intervals, the pellet was taken out for weight and size measurement. By comparing the weight and size of the same pellet at the selected time intervals, the swell parameters of PVDF-HFP in different solvents were calculated.

Figure 32:
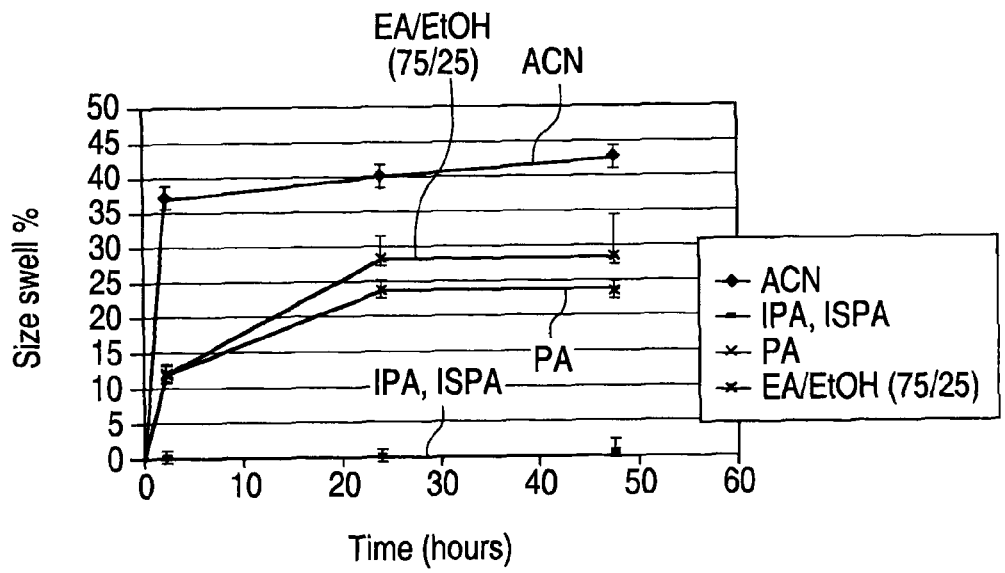
FIG. 32 shows the swell percentage of a polymer sample in various solvents obtained by measuring the size of the sample at selected times.

FIG. 32 shows the swell percentage of a polymer sample in each solvent tested obtained by measuring the size of the sample at selected times. The swell percentage was calculated by the following formula: (volume(t)−initial volume)/initial volume×100%. The polymer sample in ACN had the highest swell percentage or ratio. There was no swelling of the polymer sample in the IPA. The polymer sample in the other three solvents had swell ratios below that of ACN. The swell ratios of the sample for each of solvents appear to flatten out after about 24 hours. Other than acetonitrile, isopropyl acetate and propyl acetate resulted in larger polymer swell for samples than the mixture of ethanol and ethyl acetate.

Figure 33:
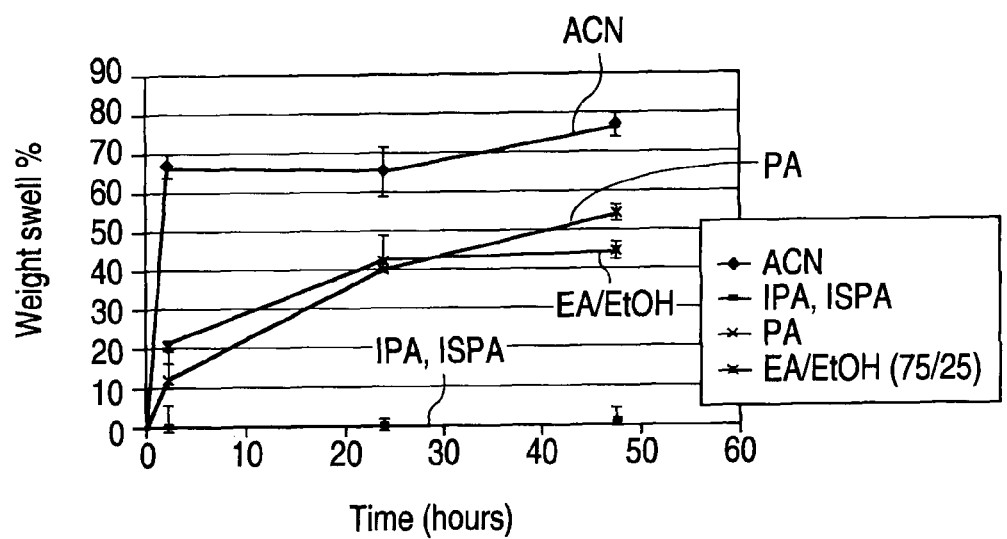
FIG. 33 shows the swell percentage of a polymer sample in various solvents obtained by measuring the weight of the sample at selected times.

FIG. 33 shows the swell percentage of polymer samples in each solvent obtained by measuring the weight at selected times. As above, the polymer samples had the largest swell ratio in acetonitrile and isopropyl alcohol did not cause any swelling in the polymer sample. As before isopropyl acetate and propyl acetate had a greater effect on polymer swelling than the mixture of ethanol and ethyl acetate.

FIGS. 32-33 show that the swell percentage obtained from the different methods of determining the swell percentage yielded different values of the swell percentage. The difference may be due to precision of polymer pellet diameter measurement and the precision of the polymer pellet weight measurement.

The removal of contaminants was studied by analyzing an extraction phase. The extraction phase refers to the mixture of the solvent and any impurities or contaminants removed or extracted from the swelled sample polymer. The extraction phase of acetonitrile, isopropyl acetate, and propyl acetate was analyzed. The extraction phase was blow-dried with a stream of heated gas. The residual remaining after the extraction phase was blow-dried included contaminants extracted from the polymer sample. The residual was analyzed by Gel Permeation Chromotography (GPC) analysis. Acetone was used to dissolve the residual impurities or contaminants for the GPC injection. A person of ordinary skill in the art is familiar with the principles of GPC analysis.

The acetonitrile extracted more residual than either isopropyl acetate or propyl acetate. Table 4 lists the results of the GPC analysis of the residual for each solvent. In Table 4, the "retention time" is the characteristic time of passage of a component through a GPC system. For the extracts from acetonitrile, a large peak retention time of 19 minutes overwrote other small insignificant peaks. For the extracted residual from isopropyl acetate and propyl acetate, the results showed a mixture of small molecular weight and large molecular weight material. The large molecular weight material corresponds to the molecular weight of PVDF-HFP, which is about 280K.

TABLE 4

Results of GPC analysis of extraction phase.

| Extraction Solvents | Retention Time | $M_w$ of the residual |
|---|---|---|
| Acetonitrile | 19 min | 63K |
| Isopropyl Acetate | 21 min | 24K |
|  | 15 min | 288K |
| Propyl Acetate | 21 min | 19K |
|  | 15 min | 278K |

Generally, it is desirable to use a solvent to purify PVDF-HVP that (1) swells and extracts a substantial amount of low molecular weight materials from the polymer and that (2) dissolves as little as possible of the polymer. The data indicates that isopropyl acetate has a favorable balance of swelling and extraction with dissolution of the polymer.

The polymer sample purified by the isopropyl acetate was analyzed after extraction to determine drying time. The polymer sample was dried in a convection oven at three different temperatures. The change in weight was determined using Thermogravimetric Analysis (TGA). Table 5 summarizes the results from TGA. The data in Table 3 indicate that drying at 85° C. or 90° C. for 24 hours will remove the solvent to an acceptable level.

TABLE 5

Results of TGA analysis of sample purified by isopropyl acetate.

| Oven Temperature (° C.) | Drying Time | Drop of Weight in TGA Test | Comments |
|---|---|---|---|
| 80 | 24 hr | 1.17% | Polymer looked normal after dry |
| 85 | 24 hr | 0.83% | Polymer looked normal after dry |
| 90 | 24 hr | 0.56% | Polymer looked normal after dry |

Stent and Coating Materials

A non-polymer substrate for a coating of an implantable medical device may be made of a metallic material or an alloy such as, but not limited to, cobalt chromium alloy (EL-GILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

In accordance with one embodiment, the composition can include a solvent and a polymer dissolved in the solvent and optionally a wetting fluid. The composition can also include active agents, radiopaque elements, or radioactive isotopes. Representative examples of polymers that may be used as a substrate of a stent or coating for a stent, or more generally, implantable medical devices include, but are not limited to, poly(N-acetylglucosamine) (Chitin), Chitosan, poly(3-hydroxyvalerate), poly(lactide-co-glycolide), poly(3-hydroxybutyrate), poly(4-hydroxybutyrate), poly(3-hydroxybutyrate-co-3-hydroxyvalerate), polyorthoester, polyanhydride, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in fabricating embodiments of implantable medical devices disclosed herein include ethylene vinyl alcohol copolymer (commonly known by the generic name EVOH or by the trade name EVAL), poly(butyl methacrylate), poly (vinylidene fluoride-co-hexafluoropropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, poly(vinyl acetate), styrene-isobutylene-styrene triblock copolymers, and polyethylene glycol.

"Solvent" is defined as a liquid substance or composition that is compatible with the polymer and is capable of dissolving the polymer at the concentration desired in the composition. Examples of solvents include, but are not limited to, dimethylsulfoxide (DMSO), chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methylpyrrolidinone, toluene, and combinations thereof.

A "wetting" of a fluid is measured by the fluid's capillary permeation. Capillary permeation is the movement of a fluid on a solid substrate driven by interfacial energetics. Capillary permeation is quantified by a contact angle, defined as an angle at the tangent of a droplet in a fluid phase that has taken an equilibrium shape on a solid surface. A low contact angle means a higher wetting liquid. A suitably high capillary permeation corresponds to a contact angle less than about 90°. Representative examples of the wetting fluid include, but are not limited to, tetrahydrofuran (THF), dimethylformamide (DMF), 1-butanol, n-butyl acetate, dimethylacetamide (DMAC), and mixtures and combinations thereof.

Examples of radiopaque elements include, but are not limited to, gold, tantalum, and platinum. An example of a radioactive isotope is $P^{32}$. Sufficient amounts of such substances may be dispersed in the composition such that the substances are not present in the composition as agglomerates or flocs.

Active Agents

Examples of active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The bioactive agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel, (e.g., TAXOL® by Bristol-Myers Squibb Co., Stamford, Conn.), docetaxel (e.g., Taxotere®, from Aventis S.A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include aspirin, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax a (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, proteins, peptides, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate agents include cisplatin, insulin sensitizers, receptor tyrosine kinase inhibitors, carboplatin, alpha-interferon, genetically engineered epithelial cells, steroidal anti-inflammatory agents, non-steroidal anti-inflammatory agents, antivirals, anticancer drugs, anticoagulant agents, free radical scavengers, estradiol, antibiotics, nitric oxide donors, super oxide dismutases, super oxide dismutases mimics, 4-amino-2,2,6,6-tetramethylpiperidine-1-oxyl (4-amino-TEMPO), tacrolimus, dexamethasone, ABT-578, clobetasol, cytostatic agents, prodrugs thereof, co-drugs thereof, and a combination thereof. Other therapeutic substances or agents may include rapamycin and structural derivatives or functional analogs thereof, such as 40-O-(2-hydroxy)ethyl-rapamycin (known by the trade name of EVEROLIMUS), 40-O-(3-hydroxy)propyl-rapamycin, 40-O-[2-(2-hydroxy)ethoxy]ethyl-rapamycin, methyl rapamycin, and 40-O-tetrazole-rapamycin.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of coating a stent, the method comprising:
   contacting a first axial end portion of a stent with a support element, while a second axial end portion of the stent is free of contact with the support element;
   applying a coating material to the second axial end portion while contacting the first axial end portion with the support element and while the second axial end portion is free of contact with the support element;
   during the applying of the coating material to the second axial end portion, inhibiting or preventing application of the coating material on the first axial end portion;
   after the applying of the coating material to the second axial end portion of the stent, pushing the stent off the support element using a shuttle sheath disposed over the support element; and
   wherein applying of the coating material to the second axial end portion is performed while the second axial end portion is free of contact with the support element and any other support element.

2. The method of claim 1, wherein the inhibiting or preventing of application of the coating material on the first axial end portion of the stent includes shielding the first axial end portion from the coating material.

3. The method of claim 1, further comprising:
   after the pushing of the stent, contacting the second axial end portion of the stent on a second support element while the first axial end portion is free of contact with the second support element;
   applying the coating material to the first axial end portion of the stent while contacting the second axial end portion with the second support element and while the first axial end portion is free of contact with the second support element; and
   during the applying of the coating material to the first axial end portion, inhibiting or preventing application of the coating material to the second axial end portion.

4. The method of claim 3, wherein the inhibiting or preventing of application of the coating material on the second axial end portion of the stent includes shielding the second axial end portion from the coating material.

5. The method of claim 3, further comprising, after the applying of the coating material to the first axial end portion of the stent, pushing the stent off the second support element using a second shuttle sheath disposed over the second support element.

6. The method of claim 3, further comprising, before the applying of the coating material to the first axial end portion of the stent, positioning a second shuttle sheath relative to the second support element to allow the contact between the second axial end portion and the second support element, wherein the second shuttle sheath is disposed over the second support element.

7. The method of claim 6, further comprising, after the applying of the coating material to the first axial end portion of the stent, pushing the stent off the second support element using the second shuttle sheath.

8. The method of claim 3, wherein the applying of the coating material to the first axial end portion is performed while the first axial end portion is free of contact with the second support element and any other support element.

9. The method of claim 1, wherein during the applying of the coating material to the second axial end portion, the first axial end portion makes contact with a portion of the support element that is untapered and cylindrical.

10. A method of coating a stent, the method comprising:
contacting a first axial end portion of a stent with a support element, while a second axial end portion of the stent is free of contact with the support element;
applying a coating material to the second axial end portion while contacting the first axial end portion with the support element and while the second axial end portion is free of contact with the support element;
during the applying of the coating material to the second axial end portion, inhibiting or preventing application of the coating material on the first axial end portion;
before the applying of the coating material to the second axial end portion of the stent, positioning a shuttle sheath relative to the support element to allow the contact between the first axial end portion of the stent and the support element, wherein the shuttle sheath is disposed over the support element; and
wherein applying of the coating material to the second axial end portion is performed while the second axial end portion is free of contact with the support element and any other support element.

11. The method of claim 10, further comprising, after the applying of the coating material to the second axial end portion of the stent, pushing the stent off the support element using the shuttle sheath.

12. The method of claim 10, wherein the inhibiting or preventing of application of the coating material on the first axial end portion of the stent includes shielding the first axial end portion from the coating material.

13. The method of claim 10, further comprising:
removing the stent from the support element after the applying of the coating material to the second axial end portion of the stent; followed by
contacting the second axial end portion of the stent on a second support element while the first axial end portion is free of contact with the second support element; and
applying the coating material to the first axial end portion of the stent while contacting the second axial end portion on the second support element and while the first axial end portion is free of contact with the second support element; and
during the applying of the coating material to the first axial end portion, inhibiting or preventing application of the coating material to the second axial end portion.

14. The method of claim 13, wherein the inhibiting or preventing of application of the coating material on the second axial end portion of the stent includes shielding the second axial end portion from the coating material.

15. The method of claim 13, further comprising, after the applying of the coating material to the first axial end portion of the stent, pushing the stent off the second support element using a second shuttle sheath disposed over the second support element.

16. The method of claim 13, wherein the applying of the coating material to the first axial end portion is performed while the first axial end portion is free of contact with the second support element and any other support element.

17. The method of claim 10, wherein during the applying of the coating material to the second axial end portion, the first axial end portion makes contact with a portion of the support element that is untapered and cylindrical.

* * * * *